United States Patent
Milligan et al.

(10) Patent No.: US 7,101,677 B1
(45) Date of Patent: Sep. 5, 2006

(54) RECEPTOR ASSAY

(75) Inventors: Graeme Milligan, Glasgow (GB); Edward Stephen Rees, Welwyn Garden City (GB)

(73) Assignee: University Court of the University of Glasgow, Glasgow (GB)

( * ) Notice: Subject to any disclaimer, the term of this patent is extended or adjusted under 35 U.S.C. 154(b) by 0 days.

(21) Appl. No.: 09/913,762

(22) PCT Filed: Feb. 18, 2000

(86) PCT No.: PCT/GB00/00585

§ 371 (c)(1), (2), (4) Date: Nov. 27, 2001

(87) PCT Pub. No.: WO00/49416

PCT Pub. Date: Aug. 24, 2000

(30) Foreign Application Priority Data

Feb. 18, 1999 (GB) ................................ 9903767.3

(51) Int. Cl.
C12Q 1/66 (2006.01)
G01N 33/53 (2006.01)

(52) U.S. Cl. .......................... 435/7.2; 435/7.21; 435/8; 435/968

(58) Field of Classification Search ................ 435/7.2, 435/7.21, 8, 968
See application file for complete search history.

(56) References Cited

U.S. PATENT DOCUMENTS 6,232,107 B1 * 5/2001 Bryan et al. ................. 435/189
6,555,339 B1 * 4/2003 Liaw et al.
6,660,844 B1 * 12/2003 Siegel et al. ................. 530/402

FOREIGN PATENT DOCUMENTS

WO  WO 97/20931  6/1997
WO  WO 98/30715  7/1998

OTHER PUBLICATIONS

U.S. Appl. No. 60/035,770, filed Jan. 7, 1997.*
U.S. Appl. No. 60/079,624, filed Mar. 27, 1998.*
Barak et al., "Internal Trafficking and Surface Mobility of a Functionality Intact $\beta_2$-Adrenergic Receptor-Green Fluorescent Protein Conjugate," *Modular Pharmacology*, 51: 177-184 (1997).
McLean et al., "Visualizing Differences in Ligand Regulation of Wild-Type and Constitutively Active Mutant Beta2-Adrenoceptor-Green Fluorescent Protein Fusion Proteins," *Molecular Pharmacology*, 56: 1182-1191 (Dec., 1999) (Abstract).
International Preliminary Examination Report; date of mailing: May 1, 2001.
Chen et al., "A Colorimetric Assay for Measuring Activation of $G_s$- and $G_q$-Coupled Signaling Pathways," *Analytical Biochemistry*, 226: 349-354 (1995).

Gether et al., "Agonists Induce Conformational Changes in Transmembrane Domains III and VI of the $\beta_2$ Adrenoceptor," *The EMBO Journal*, 16(22): 6737-6747 (1997).
Gudermann et al., "Diversity and Selectivity of Receptor—G Protein Interaction," *Annual Review of Pharmacology and Toxicology*, 36: 429-459 (1996). ABSTRACT.
Haas et al., "Codon Usage Limitation in the Expression of HIV-1 Envelope Glycoprotein," *Current Biology*, 6(3): 315-324 (1996).
Javitch et al., "Constitutive Activation of the $\beta_2$ Adrenergic Receptor Alters the Orientation of Its Sixth Membrane-Spanning Segment," *The American Society for Biochemistry and Molecular Biology, Inc.*, 272(30): 18546-18549 (Jul. 25, 1997).
Leurs et al., "Agonist-Independent Regulation of Constitutively Active G-Protein-Coupled Receptors," *TIBS* 23, 418-422 (Nov. 1998).
Samama et al., "A Mutation-Induced Activated State of the $\beta_2$-Adrenergic Receptor," *The Journal of Biological Chemistry*, 268(7): 4625-4636 (1993).
Samama et al., "Negative Antagonists Promote an Inactive Conformation of the Beta 2-Adrenergic Receptor," *American Society for Pharmacology and Experimental Therapeutics*, 45(3): 390-394 (1994). ABSTRACT.
A. Scheer & S. Cotecchia, "Constitutively Active G Protein-Coupled Receptors: Potential Mechanisms of Receptor Activation," *J. of Receptor & Signal Transduction Research*, 171(1-3): 57-73 (1997).
Stratowa et al., "Use of a Luciferase Reporter System for Characterizing G-Protein-Linked Receptors," *Current Opinion in Biotechnology*, 6: 574-581 (1995).
D. Walker & M. De Waard, "Subunit Interaction Sites in Voltage-Dependent $Ca^{2+}$ Channels: Role in Channel Function," *Trends Neurosc.*, 21: 148-154 (1998).
S. Wang & T. Hazelrigg, "Implications for bcd mRNA Localization from Spatial Distribution of exu Protein in *Drosophila* Oogenesis,"*Letters to Nature*, 369: 400-403 (1994).
Wise et al., "Interactions of the $\alpha_{2A}$-Adrenoceptor with Multiple $G_i$-Family G-Proteins: Studies with Pertussis Toxin-Resistant G-Protein Mutants," *Biochem. J.*, 321: 721-728 (1997).
Chalfie et al.; *GFP Green Fluorescent Protein; Properties, Applications and Protocols*, A. John Wiley & Sons, Inc. Publication (1998).

* cited by examiner

*Primary Examiner*—David Saunders
(74) *Attorney, Agent, or Firm*—Carol L. Francis; Bozicevic, Field & Francis LLP

(57) ABSTRACT

The present invention relates to receptor/reporter fusion protein based assays for detecting the effect test compounds have on a particular membrane receptor, as well as to receptor/reporter fusion proteins for use in such assays and compounds identified by the assays as having interesting/useful effects. Suitable membrane receptors are growth factor receptors, cytokine receptors, ion channels and integrins including any subtypes, mutants, homologs and chimeric forms of such receptors. The assay may be to study G-protein coupled receptors (GPCRs).

20 Claims, 22 Drawing Sheets

(−) Betaxolol (+) Betaxolol

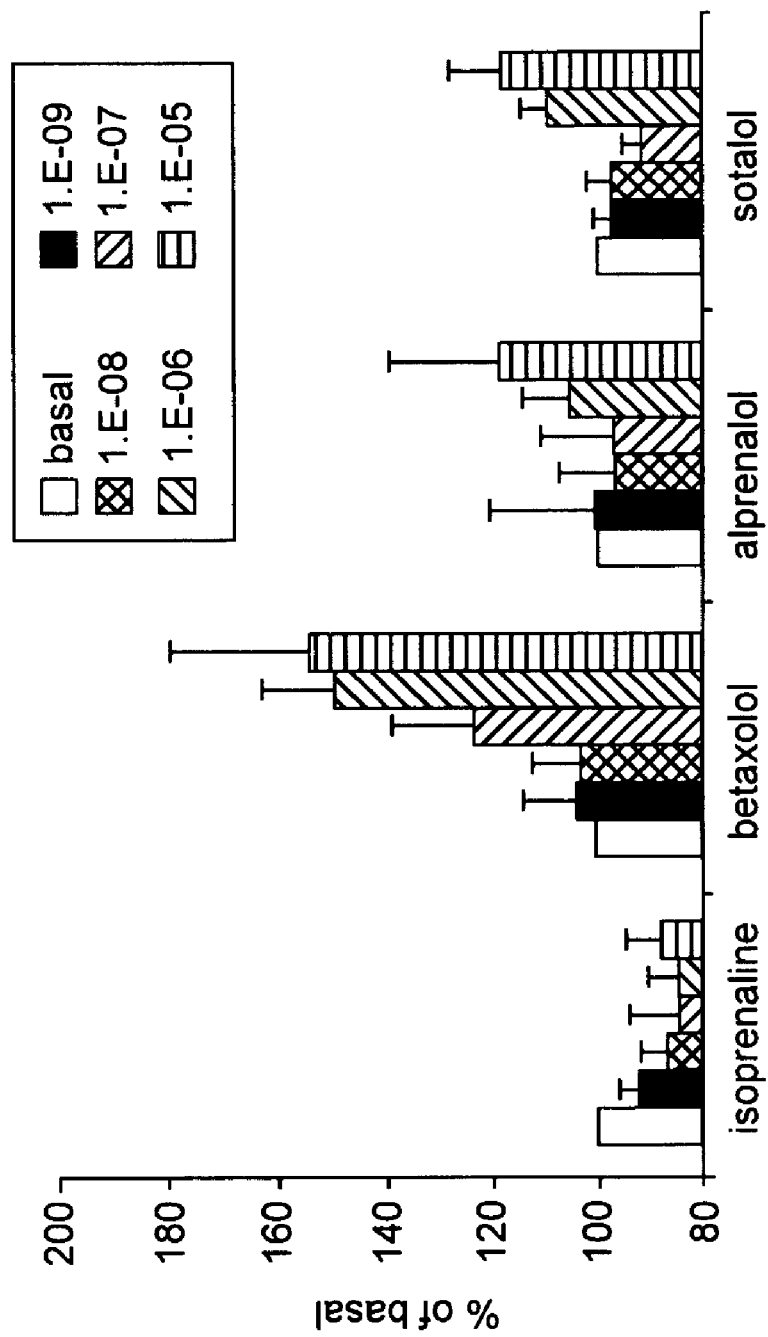

b)

d)

a)

c)

Figure 1:
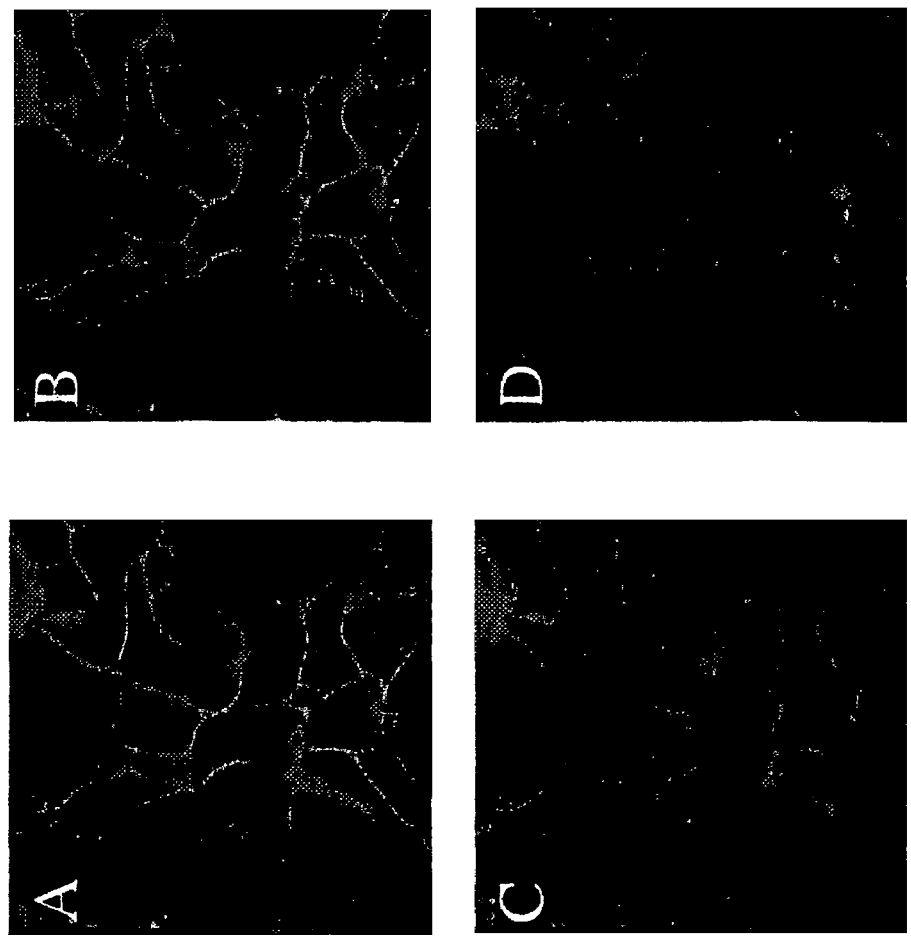

| CAM β₂AR | Renilla Luciferase |

(−) Antagonist                (+) Antagonist

Upregulation monitored by increased luciferase activity in cells

A

B

SEQUENCE LISTING

<160> NUMBER OF SEQ ID NOS: 17

<210> SEQ ID NO 1
<211> LENGTH: 63
<212> TYPE: DNA
<213> ORGANISM: Artificial sequence
<220> FEATURE:
<223> OTHER INFORMATION: Primer

<400> SEQUENCE: 1
aaaaaaaagc ttgccaccat ggactacaag gacgacgatg ataagggggca acccgggaac    60 ggc    63

<210> SEQ ID NO 2
<211> LENGTH: 36
<212> TYPE: DNA
<213> ORGANISM: Artificial sequence
<220> FEATURE:
<223> OTHER INFORMATION: Primer

<400> SEQUENCE: 2
aaaaaggatc ctcccgccag cagtgagtca tttgta    36

<210> SEQ ID NO 3
<211> LENGTH: 27
<212> TYPE: DNA
<213> ORGANISM: Artificial sequence
<220> FEATURE:
<223> OTHER INFORMATION: Primer

<400> SEQUENCE: 3
atggactaca aggacgacga tgataag    27

<210> SEQ ID NO 4

-continued

<210> SEQ ID NO 4
<211> LENGTH: 32
<212> TYPE: DNA
<213> ORGANISM: Artificial sequence
<220> FEATURE:
<223> OTHER INFORMATION: Primer

<400> SEQUENCE: 4
aaaaaggatc cagtaaagga gaagaacttt tc                                    32

<210> SEQ ID NO 5
<211> LENGTH: 33
<212> TYPE: DNA
<213> ORGANISM: Artificial sequence
<220> FEATURE:
<223> OTHER INFORMATION: Primer

<400> SEQUENCE: 5
tgctctagat tatttgtata gttcatccat gcc                                   33

<210> SEQ ID NO 6
<211> LENGTH: 28
<212> TYPE: DNA
<213> ORGANISM: Artificial sequence
<220> FEATURE:
<223> OTHER INFORMATION: Primer

<400> SEQUENCE: 6
ggaaggtacc agtaaaggag aagaactt                                         28

<210> SEQ ID NO 7
<211> LENGTH: 36
<212> TYPE: DNA
<213> ORGANISM: Artificial sequence
<220> FEATURE:
<223> OTHER INFORMATION: Primer

<400> SEQUENCE: 7
tgctctagat tatttgtata gttcatccat gccatg                                36

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
gacggtacct ctaaaatgaa tcccgat                                          27

<210> SEQ ID NO 9
<211> LENGTH: 26
<212> TYPE: DNA
<213> ORGANISM: Artificial sequence
<220> FEATURE:
<223> OTHER INFORMATION: Primer

<400> SEQUENCE: 9
gtccctggta ccaaagtgcc cgggtg                                           26

<210> SEQ ID NO 10
<211> LENGTH: 10
<212> TYPE: PRT
<213> ORGANISM: Artificial sequence
<220> FEATURE:
<223> OTHER INFORMATION: Mutant PAR1 sequence

<400> SEQUENCE: 10

```
Ala Gly Ala Gly Ala Gly Ala Gly Gly Ala
1               5                   10
```

<210> SEQ ID NO 11
<211> LENGTH: 4
<212> TYPE: PRT
<213> ORGANISM: Artificial sequence
<220> FEATURE:
<223> OTHER INFORMATION: Mutant PAR1 sequence

<400> SEQUENCE: 11

```
Ala Gly Ala Gly
1
```

<210> SEQ ID NO 12
<211> LENGTH: 6
<212> TYPE: PRT
<213> ORGANISM: Artificial sequence
<220> FEATURE:
<223> OTHER INFORMATION: Mutant PAR1 sequence

<400> SEQUENCE: 12

```
Ala Gly Ala Gly Gly Ala
1               5
```

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
gcgcagagcc cgggacaatg                                              20

<210> SEQ ID NO 14
<211> LENGTH: 33
<212> TYPE: DNA
<213> ORGANISM: Artificial sequence
<220> FEATURE:
<223> OTHER INFORMATION: Primer

<400> SEQUENCE: 14
gctggatcct tttccgaagt taacagcttt ttg                               33

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
cagtttgggt ctgaattgtg tc                                           22

<210> SEQ ID NO 16
<211> LENGTH: 34
<212> TYPE: DNA
<213> ORGANISM: Artificial sequence
<220> FEATURE:
<223> OTHER INFORMATION: Primer

<400> SEQUENCE: 16
ctttcaaggc tagggtcgtc acgacctcgt ccgc                              34

```
-continued

<210> SEQ ID NO 17
<211> LENGTH: 41
<212> TYPE: DNA
<213> ORGANISM: Artificial sequence
<220> FEATURE:
<223> OTHER INFORMATION: Primer

<400> SEQUENCE: 17
ccggtgcagg aggtgcaaaa atggatacct gctctagtaa c                           41
```

RECEPTOR ASSAY

RELATED APPLICATIONS

This application claims priority under 35 U.S.C. § 371 from PCT Application No. PCT/GB00/00585, filed in English on Feb. 18, 2000, which claims the benefit of Great Britain Application Serial No. 9903767.3, filed on Feb. 18, 1999, the disclosures of which are incorporated by reference herein in their entireties.

The present invention relates to receptor/reporter fusion protein based assays for detecting an effect test compounds have on a particular membrane receptor, as well as to receptor/reporter fusion proteins for use in such assays and compounds identified by the assays as having interesting/useful effects.

Traditional protocols for the measurement of ligand activity at receptors such as G-protein coupled receptors (GPCRs) have relied upon a number of biochemical techniques. These include radioligand binding analysis in which the ability of a test compound to displace the binding of a known radioligand is determined, and a number of functional assays in which the ability of a test compound to activate or inhibit a specific signal transduction event is measured.

Functional assays of ligand activity at GPCRs expressed in mammalian cells include the measurement of the rate of guanine nucleotide exchange at the activated G-protein alpha sub-unit (Wise et al., 1997), the measurement of the changes in the level of one of a plethora of intracellular second messenger metabolites, such as cAMP, calcium, or inositol phosphates (Guderman et al., 1996), or the activation or inhibition of an ion channel (Walker and de Waard, 1998). In recent years these assays have been supplemented by the development of reporter gene systems for the study of GPCR signal transduction (Stratowa et al., 1995; Alam and Cook, 1990), as well as a number of other mammalian cell, yeast or *Xenopus melanophore* based assays.

The *Aequorea victoria* photoprotein GFP (Green Fluorescent Protein) is a 238 amino acid protein that emits green light with an emission maximum of 509 nm upon fluorescent excitation at 488 nm. Unlike other bioluminescent reporter proteins no additional substrates or cofactors are required for light emission (Chen et al., 1995). GFP fluorescence is stable and has been measured non-invasively in living cells of many species including mammalian cells, *drosophila, C. elegans*, yeast and *E. coli*. GFP fluorescence can be detected by fluorimetry, by FACS and by microscopy. As there is no assay reagent or assay protocol the attractiveness of GFP as a reporter protein is cost, together with the speed and simplicity of the assay (Chalfie and Kain, 1998).

The availability of the cDNA sequence for GFP has resulted in the generation and characterisation of several GFP mutants with enhanced fluorescence emission. Mutation of the serine at amino acid 65 to threonine has resulted in the generation of a protein with a 6-fold increase in the intensity of fluorescence emission (Haas et al., 1996). Furthermore, the presence of the Ser65Thr and the mutation of the phenylalanine residue at position 64 to leucine has resulted in a 35-fold increase in fluorescence intensity (Haas et al., 1996). In addition, a number of novel mutants of GFP have also been identified with altered excitation or emission characteristics. For example mutation of the tyrosine residue at position 66 to histidine has generated a protein with blue fluorescence emission, the so-called blue fluorescent protein (BFP) with a $\lambda_{max}$ for excitation of 458 nm and for emission of 480 nm (Chalfie and Kain, 1998). These and many other variants of GFP protein are now commercially available.

GFP has been widely used in fusion proteins to assess protein trafficking, and subcellular localisation of recombinantly expressed proteins (Wang and Hazelrigg, 1994). Recently, a number of groups have described the creation and use of GPCR-GFP fusion proteins to monitor receptor internalisation and recycling following agonist treatment. For example a fusion protein between the $\beta_2$-adrenoceptor and GFP has been used to monitor receptor expression, localisation at the plasma membrane and internalisation following agonist stimulation (Barak et al., 1997).

In recent years a number of studies have described the introduction of specific mutations into GPCRs that result in agonist-independent activation of a signal transduction cascade by the mutant GPCR when expressed in mammalian cells (Scheer and Cotecchia, 1997, Leurs et al., 1998). This phenomena has been described as constitutive activity, and such mutant receptors termed constitutively active mutant (CAM) receptors. Such experiments have generally been considered to shed light on possible structural alterations in the GPCR which occur upon agonist-binding to result in activation of a cognate G protein and thus regulation of the activity of downstream effector enzymes. Such strategies appear to possess validity because, in the case of the $\beta_2$-adrenoceptor for example, one of the structural modifications associated with agonist binding to the wild type GPCR is a movement of transmembrane helix 6 which can be measured by the positioning of residue $Cys^{285}$ (Gether et al., 1997a). In a CAM form of this GPCR this same Cys residue is closer to the ligand binding pocket than in the ligand-unoccupied wild type receptor (Javitch et al., 1997).

Perhaps the most studied of the CAM GPCRs is a form of the human $\beta_2$-adrenoceptor in which a short segment of the C-terminal region of the third intracellular loop was replaced with the corresponding region from the $\alpha_{1B}$-adrenoceptor (Samama et al., 1993, Samama et al., 1994).

The present invention is based in part on investigations on the possibility of developing the phenomena of ligand stabilisation of a CAM GPCR to lead to an increase in receptor number at the cell surface, as an assay system for ligand activity at such a receptor. As a model system the present applicants describe the stability and regulation, by a series of inverse agonist ligands, of a CAM $\beta_2$-adrenoceptor which has had the 27 kDa GFP added in-frame at the C-terminal. The present applicants have measured ligand efficacy by determining the ability of each ligand to cause a change in the cellular distribution of the GPCR-GFP fusion protein or to cause an alteration in total cellular fluorescence. Furthermore the present applicants have examined the effect of a series of specific agonists on the cellular distribution, and total cellular fluorescence, of cells expressing a WT $\beta_2$-adrenoceptor/GFP fusion protein as a screening system for agonist ligands at this receptor.

Thus, in a first aspect the present invention provides an assay for detecting an effect a compound has on a membrane receptor/reporter fusion protein, comprising the steps of:

a) adding the compound to a cell comprising said membrane receptor/reporter fusion protein; and b) detecting any change of said receptor/reporter fusion protein.

Typically the assay may be used to screen compounds for their effect on particular membrane receptors. Compounds identified as having an effect on a particular membrane receptor may be useful, for example, in modulating the activity of wild type and/or mutant membrane receptors;

may be used in elaborating the biological function of particular membrane receptors; and/or may be used in screens for identifying compounds that disrupt normal membrane receptor interactions, or can in themselves disrupt such interactions.

The assay is particularly suited for the detection of compounds which serve as inverse agonists, antagonists or agonists of the membrane receptor. The term inverse agonist is understood to mean a compound which when it binds to a receptor, selectively stabilises and thus enriches the proportion of a receptor in a conformation or conformations incapable of inducing a downstream signal. Agonist is understood to mean a compound which when it binds to a receptor selectively stabilises and thus enriches the proportion of the receptor in a conformation or conformations capable of inducing a downstream signal. Antagonist is understood to mean a compound which when it binds to a receptor has no selective ability to enrich either active or inactive conformations and thus does not alter the equilibrium between them.

The term compound is understood to include chemicals as well as peptides and/or proteins.

The present invention also therefore relates to inverse agonists, antagonists or agonists of receptor proteins identified using the assays according to the present invention and to the use of such agonists, antagonists or agonists in study receptor function, or therapy.

The assay may be applied to a variety of membrane receptors, such as growth factor receptors, cytokine receptors, ion channels and integrins. The assay is however particularly suited to studying the effects of compounds on G-protein coupled receptors (GCPRs).

The term receptor as used herein is intended to encompass subtypes of the named receptors, and mutants, such as constitutively active mutants, homologs thereof, and chimeric receptors including the nucleic acid encoding such receptors. Chimeric receptors as used herein refers to receptors which may be formed comprising parts of mammalian receptors found from different sources.

Generally speaking any G protein coupled receptor, and the DNA sequences encoding such receptors may be used in assays of the present invention. Typical G protein coupled receptors are for example dopamine receptors, muscarinic cholinergic receptors, α-adrenergic receptors, β-adrenergic receptors, opiate receptors, cannabinoid receptors and serotonin receptors.

The membrane receptors mentioned herein are typically modified by the fusion of a reporter protein to the receptor. Typically nucleic acid encoding the reporter protein, such as Green Fluorescent Protein (GFP) may be fused in-frame to an end, that is the 5' or 3' end, of a gene encoding the particular receptor. In this manner, on expression of the gene, the reporter protein is functionally expressed and fused to the N-terminal or C-terminal end of the receptor. Modification of the receptor is such that the functionality of the membrane receptor remains substantially unaffected by fusion of the reporter protein to the receptor.

As mentioned previously GFP emits green light upon fluorescent excitation. Detection of this green light may be carried out for example by fluorimetry, FACS and by microscopy techniques well known to one skilled in the art. In this manner localisation and/or quantification of a membrane receptor may be determined.

The present invention in a further aspect therefore also relates to novel membrane receptor/reporter fusion proteins for use in the disclosed assays and their nucleic acid constructs, such as a constitutively active $\beta_2$-adrenoreceptor/GFP fusion protein and $\beta_2$-adrenoreceptor/GFP gene fusion. Although it might be anticipated that attachment of the GFP 27 KDa polypeptide to the end of a receptor such as GPCR might significantly interfere with receptor function, it has been previously reported that GPCRs modified in this manner display unaltered pharmacology and remain able to interact with G proteins to initiate second messenger regulation. For example a receptor/reporter fusion protein may be provided in which the C-terminus of a receptor is linked directly to the N-terminus of a reporter protein. Minor modification may be carried out to the protein sequence, for example, an epitope tag may be added to the N-terminus of the receptor and/or the terminal methionine of the reporter gene removed. Many such modifications may be envisaged by the skilled addressee providing the functionality of the receptor/reporter fusion protein remains substantially unaffected.

The nucleic acid constructs of the present invention comprise nucleic acid, typically DNA, encoding the particular receptor to which is fused, in-frame, the appropriate gene encoding the reporter protein. Generally speaking the nucleic acid constructs are expressed in the cells being tested by means of an expression vector. Typically, although not exclusively the cells are of mammalian origin and the expression vector chosen is one which is suitable for expression in the particular cell type.

An expression vector is a replicable DNA construct in which the nucleic acid is operably linked to suitable control sequences capable of effecting the expression of the membrane receptor/reporter fusion in the particular cell. Typically control sequences may include a transcriptional promoter, an optional operator sequence to control transcription, a sequence encoding suitable mRNA ribosomal binding sites, and sequences which control the termination of transcription and/or translation. Typical expression vectors may include for example plasmids, bacteriophages or viruses and such vectors may integrate into the host's genome or replicate automonously in the particular cell.

In order for the particular cell to express the receptor/reporter fusion protein the cell must be transformed by the appropriate expression vector. "Transformation", as used herein, refers to the introduction of a heterologous polynucleotide fragment into a host cell, irrespective of the method used, for example direct uptake, transfection or transduction.

The present invention therefore also relates to cells which have been transformed by nucleic acid constructs comprising receptor/reporter fusions of the present invention and express the receptor/reporter fusion protein.

In addition to the Green Fluorescent Protein (GFP) similar receptor/reporter fusion protein constructs may be made using other coloured varients of GFP such as the Blue Fluorescent Protein, the Yellow Fluorescent Protein or the Cyan Fluorescent Protein (Chalfie and Kain, 1998).

Similar receptor/reporter fusions may also be generated using other reporter proteins such as firefly (*Photinus pyralis*) luciferase (Alam and Cook, 1990). The construction of a GPCR/firefly luciferase fusion would enable the detection of compound activity using firefly luciferase activity as the read-out with detection for example in a microplate luminometer or using a CCD imaging system. Firefly luciferase assays are highly sensitive and are amenable to assay in miniturised plate formats and for detection by CCD imaging (Suto and Ignar, 1997). In addition to GFP or firefly luciferase similar receptor/reporter fusions may be gener ated using any reporter enzyme including *Renilla reniformis* (sea pansy) luciferase (DeWet et al., 1987), secreted placental alkaline phosphatase (SEAP) (Lorenz et al., 1991), β-lactamase (Moore et al., 1997) and β galactosidase (Henthorn et al., 1988).

Any change of said membrane receptor/reporter fusion protein as a result of adding the compound may be detected for example as a change in cellular localisation of the receptor/reporter fusion protein, or semi-quantitatively by the synthesis or degradation of said receptor/reporter fusion protein. Detection of any changes may easily be carried out with cells placed on the surface of a microscope slide or the like. However, the assays of the present invention may conveniently be carried out on cells placed in a well of a microtitre plate or the like, such as a conventional 96-well plate.

A further modification to the assay described herein may be achieved for example by taking advantage of the route of internalisation and degradation of the PAR1 receptor. The protease activated receptor PAR1 mediates thrombin signalling. Unlike classic GPCRs such as the $\beta_2$-adrenoceptor which possess reversibly bound ligands, PAR1 (and other PAR family members), are activated following proteolytic cleavage of the N-terminus of the receptor protein by proteases such as thrombin to generate a new amino terminus that serves as a "tethered ligand", binding intramolecularly to the body of the receptor to initiate receptor signalling (Vu et al., 1991a and 1991b). As with other GPCRs, following ligand activation PAR1 becomes rapidly phosphorylated and uncoupled from signalling. However, unlike classic GPCRs, PAR1 is sorted largely to the lysosomes to result in protein degradation (Trejo et al., 1998; Shapiro and Coughlin, 1998). Trafficking of activated PAR1 to the lysosomal rather than the endosomal compartment appears to be mediated entirely by the C-terminal tail of PAR1 (Trejo and Coughlin, 1999). The Substance P receptor (SPR) is activated by the peptide ligand substance P, internalised and recycled to the plasma membrane as observed for the WT $\beta_2$-adrenoceptor-GFP fusion protein. However, exchanging the carboxyl cytoplasmic tail of the SPR for that of the PAR1 receptor resulted in the creation of an SPR/PAR1 fusion protein, which when activated by the ligand Substance P, became targeted to the lysosome for proteolytic degradation, rather than to the endosome for recycling to the plasma membrane (Trejo and Coughlin, 1999).

Thus it may be expected that a fusion protein comprising the substance P receptor, the $\beta_2$-adrenoceptor or any other GPCR, in which the cytoplasmic C-terminal tail of the receptor was replaced with the cytoplasmic C-terminal tail of the PAR1 receptor, would be internalised into lysosomes following agonist treatment to result in the degradation of the receptor protein. If this fusion protein also contained GFP, or any other reporter protein, fused in-frame onto the carboxyl terminus of the PAR1 receptor cytoplasmic C-terminal tail then agonist treatment would result in a loss of reporter signal as a result of lysosomal degredation of receptor protein. To assay for compounds with antagonist or inverse agonist activity cells would be pretreated with antagonist for a period of time prior to the addition of agonist. The antagonist would prevent agonist binding to the receptor, and so prevent agonist mediated degradation of receptor protein. Using GFP as the reporter protein this may be detected either by confocal microscopy of individual or groups of cells, or in microplate formats using a appropriate microplate fluorimeter. Using firefly luciferase as the reporter protein receptor changes could be assessed following the assay of firefly luciferase activity using either microplate luminometry or by CCD imaging.

The present invention will now be further described by way of example only, with reference to the following figures which show:

FIG. 1 shows plasma membrane location of WT $\beta_2$-adrenoceptor-GFP and internalisation in response to isoprenaline. The WT $\beta_2$-adrenoceptor-GFP was expressed stably in HEK293 cells and individual clones isolated. A patch of cells were imaged in the confocal microscope in the absence of agonist (A) and following addition of 10 µM isoprenaline for 5 (B), 10 (C) and 30 (D) min.

Figure 2:
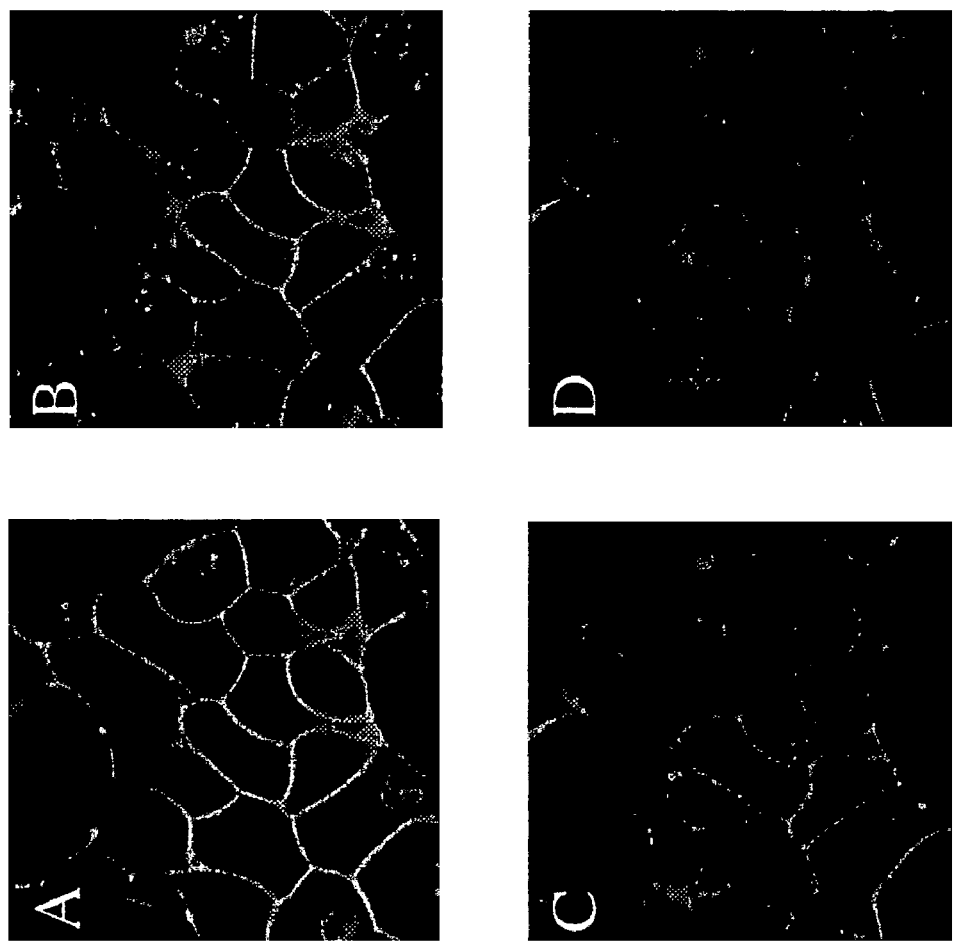

FIG. 2 shows recycling of WT $\beta_2$-adrenoceptor-GFP to plasma membrane following addition of alprenolol. A patch of HEK 293 cells stably expressing the WT $\beta_2$-adrenoceptor-GFP fusion protein were imaged in the confocal microscope in the absence of agonist (A) or following addition of isoprenaline (10 µM) for 30 min (B). Following washing to remove isoprenaline, alprenolol (10 µM) was added for 30 (C) or 40 (D) min.

Figure 3:
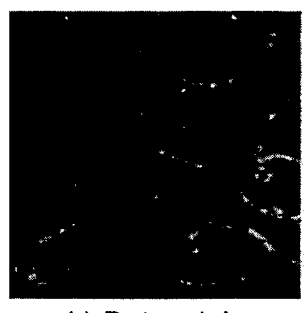
Figure 3:
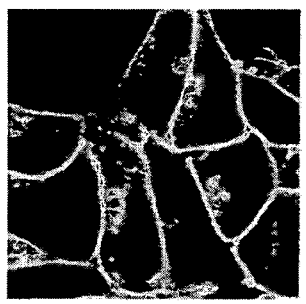
Figure 3:
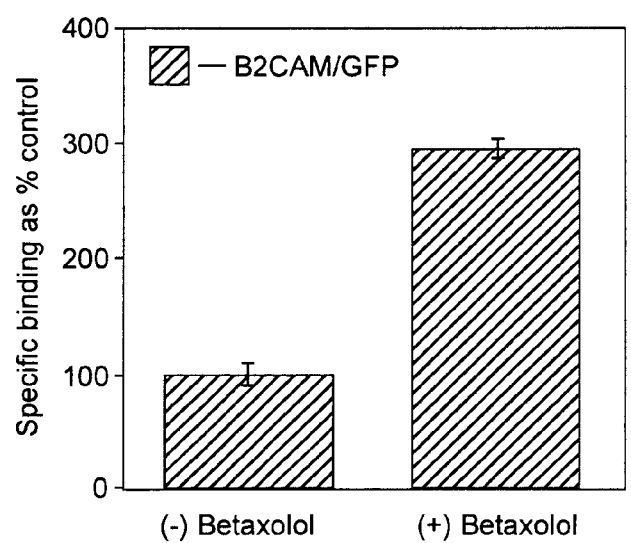

FIG. 3 shows expression of CAM $\beta_2$-adrenoceptor-GFP and upregulation by betaxolol. A CAM $\beta_2$-adrenoceptor-GFP construct was expressed stably in HEK293 cells and individual clones isolated. (a) Cells of a single clone were grown on glass coverslips in the absence (Upper panel) or presence (Lower panel) or betaxolol (10 µM) for 24 hr. These cells were then visualised. (b) Cells of this clone which were untreated or treated with betaxolol (10 µM) and then washed were used to measure the specific binding of [$^3$H]DHA in intact cells ([$^3$H]DHA is a lipophillic antagonist which crosses the plasma membrane and thus provides a measure of total cell levels of $\beta_2$-adrenoceptor binding sites).

Figure 4:
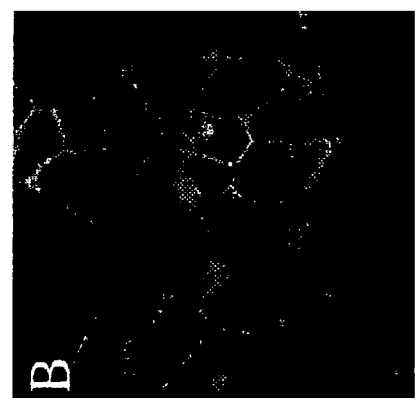
Figure 4:
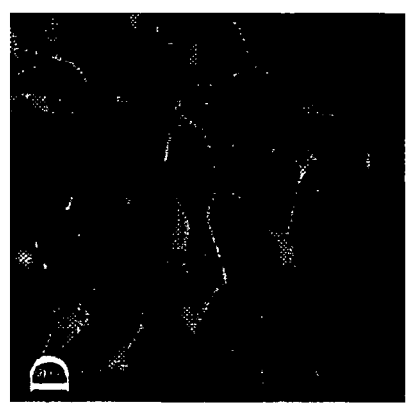
Figure 4:
Figure 4:

FIG. 4 shows upregulation of CAM $\beta_2$-adrenoceptor-GFP by other β-adrenoceptor ligands. HEK 293 cells stably expressing the CAM β2-adrenoceptor-GFP expressing cells of FIG. 3 were exposed to no ligand (A), carvedilol (B), Labetolol (C) or ICI118551 (D) (each at 1 µM) for 24h. The cells were then imaged in the confocal microscope.

Figure 5:
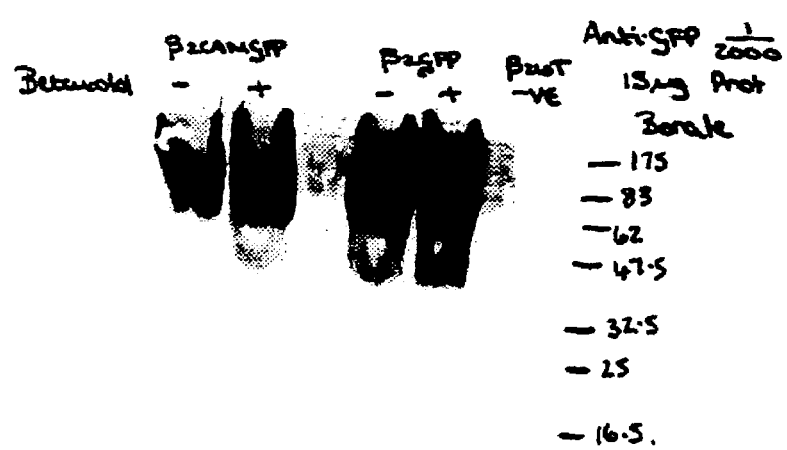

FIG. 5 shows upregulation of CAM $\beta_2$-adrenoceptor-GFP but not WT $\beta_2$-adrenoceptor-GFP by betaxolol. Membrane fractions were prepared from HEK 293 cells stably expressing either the CAM $\beta_2$-adrenoceptor-GFP or the WT $\beta_2$-adrenoceptor-GFP fusion protein which had been maintained for 24 hours in the absence or presence of betaxolol (10 µM) and subjected to SDS-PAGE. Following transfer to nitrocellulose, the samples were immunoblotted using an polyclonal anti-GFP antibody to assess the level of fusion protein in these membranes.

Figure 6A:
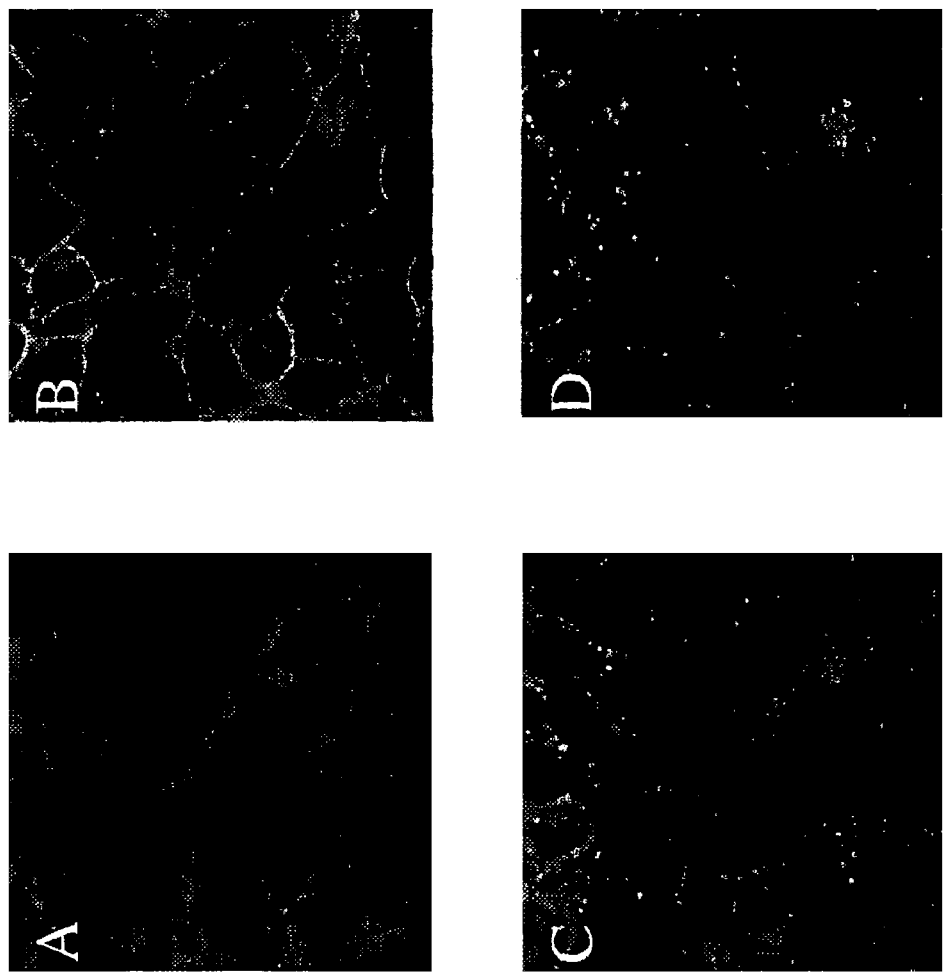

FIG. 6 shows internalisation of upregulated CAM $\beta_2$-adrenoceptor-GFP by isoprenaline (a) CAM $\beta_2$-adrenoceptor-GFP expressing cells were untreated (A) or exposed to betaxolol (10 µM, 24h) (B–D). Following betaxolol treatment the cells were washed and isoprenaline (10 µM) added for 0 (B), 10 (C) or 30 (D) min. (b) Cells as in FIG. 6*a* were untreated, exposed to betaxolol (10 µM, 24h) or exposed to betaxolol followed by further exposure to isoprenaline for 30 min. Intact cells were then used to measure the specific binding of [$^3$H]CGP12177 ([$^3$H]CGP12177 is a hydrophillic ligand which does not penetrate the plasma membrane and in these conditions records only cell surface receptors).

FIG. 7*a* shows the effect of various inverse agonists/antagonists on the level of fluorescence in CAM $\beta_2$-adrenoceptor-GFP determined by microtitre plate fluorimetery. Changes in fluorescence were measured on Spectrofluor Plus fluorimeter using cells plated in a 96 well plate. The graph shows the concentration responses to isoprenaline, betaxolol, alprenalol or sotalol after 22 h drug contact. Values are the mean percentages of basal of at least 3 experiments performed in duplicate ±SEM.

Figure 7B:
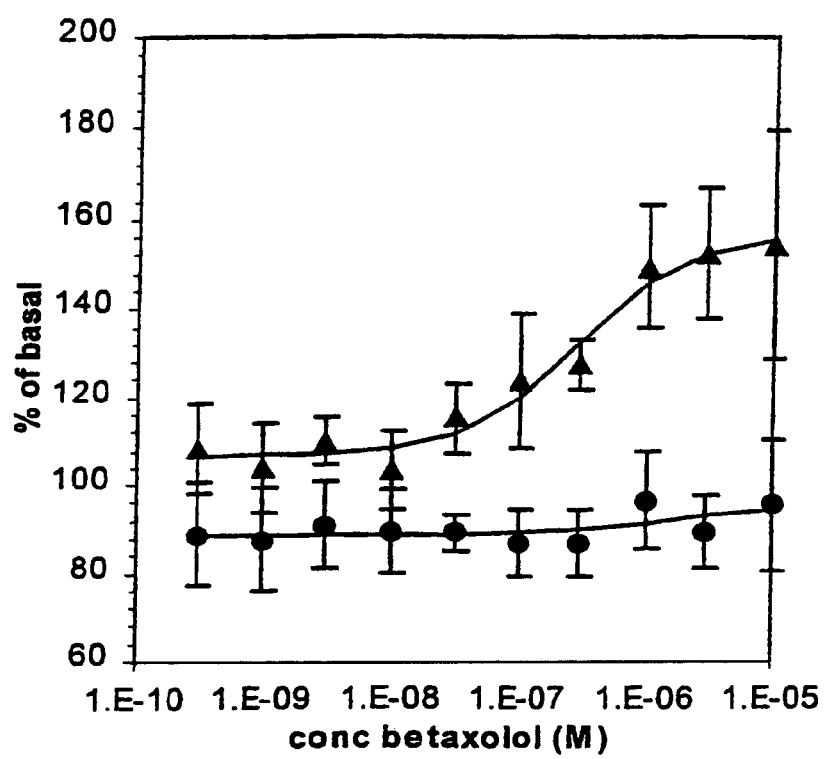

FIG. 7b shows the concentration-dependence of the upregulation of CAM $\beta_2$-adrenoceptor-GFP by betaxolol determined by microtitre plate fluorimetry. Changes in fluorescence were measured on Spectrofluor Plus fluorimeter using cells plated in a 96 well plate. The graph shows a dose response curve to betaxolol at time 0 h (●) and after 22 h (▲). Values are the mean percentages of basal of 6 experiments performed in duplicate ±SEM.

Figure 7C:
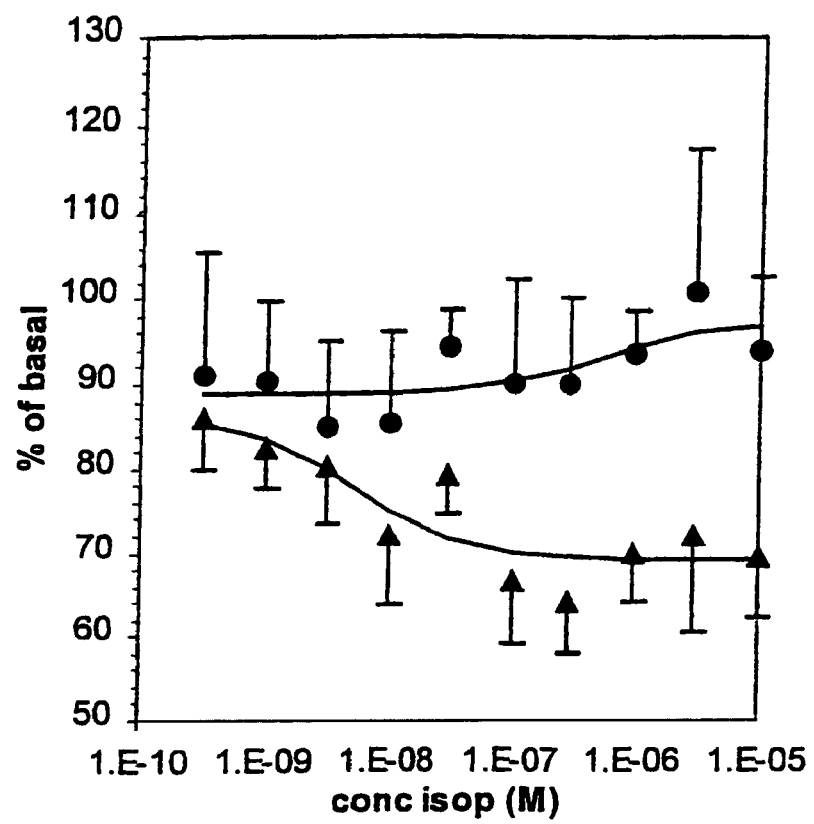

FIG. 7c shows the concentration dependence of the downregulation of $\beta_2$-adrenoceptor-GFP by Isoprenaline determined by microtitre plate fluorimetry. The graph shows a dose response curve to isoprenaline at time 0 h (●) and after 22 h (▲) Values are the mean percentages of basal of 6 experiments performed in duplicate ±SEM.

Figure 8:
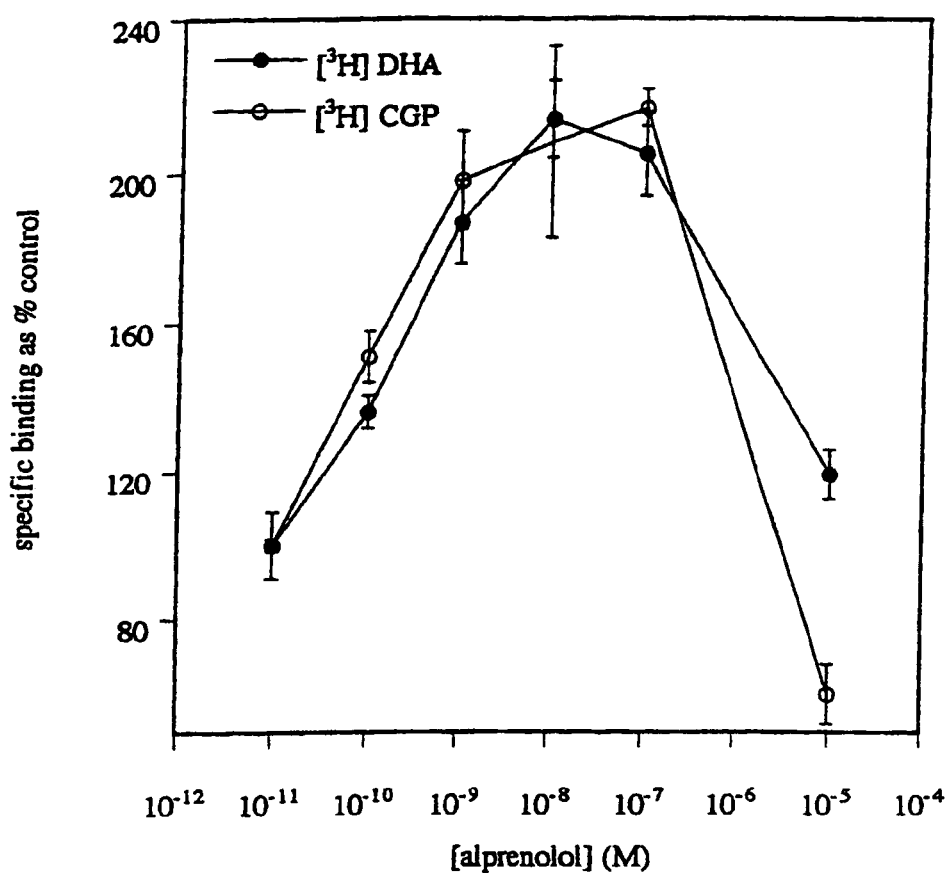

FIG. 8 shows the concentration dependence of the upregulation by of CAM $\beta_2$-adrenoceptor-GFP by alprenolol. binding studies: CAM $\beta_2$-adrenoceptor-GFP expressing cells were untreated or exposed to varying concentrations of alprenolol for 24h. They were subsequently washed and intact cell specific binding of single concentrations of either [$^3$H]DHA or [$^3$H]CGP12177 measured to ascertain levels of total cell receptor and cell surface receptor respectively.

FIG. 9

Location of mutations which imbue constitutive activation of phosphoinositidase C activity to the $\beta_{1b}$-adrenoceptor. A ribbon diagram of the primary diagram of the primary sequence of the hamster $\alpha_{1b}$-adrenoceptor is displayed. The constitutively active mutant used herein (3CAM) has the following (R288K, K290H, A293L) alterations to the wild type sequence.

FIG. 10

Upregulation of the 3CAM but not wild type hamster $\alpha_{1b}$-adrenoceptor by sustained antagonist/inverse agonist challenge. Cells expressing either the 3CAM (10A) or wild type (10B) hamster $\alpha_{1b}$-adrenoceptor grown on glass cover slips were treated with vehicle (a), phentolamine (b), WB4101 (c) or HV723 (d) (all at 1 μM) for 24h. The cells were then visualised on a confocal microscope.

Figure 10A:
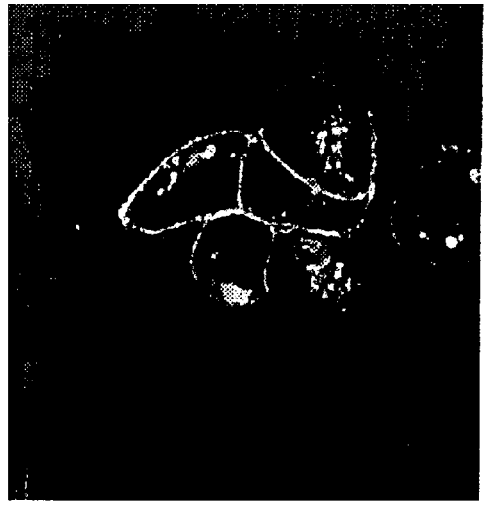
Figure 10A:
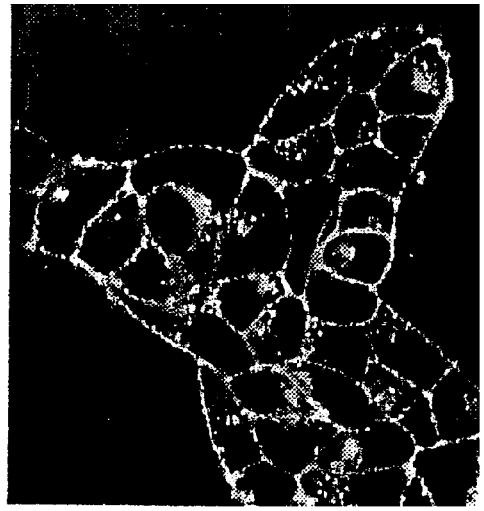
Figure 10A:
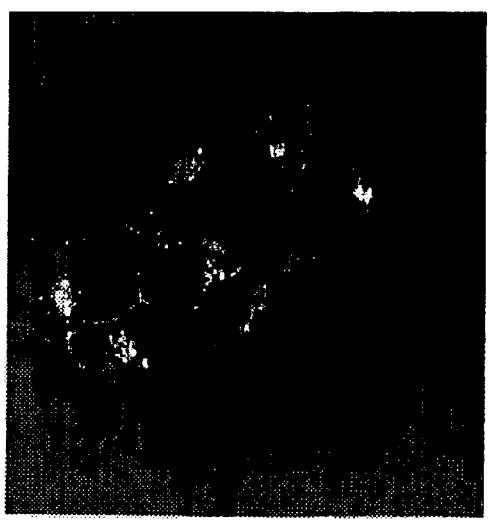
Figure 10A:
Figure 10B:
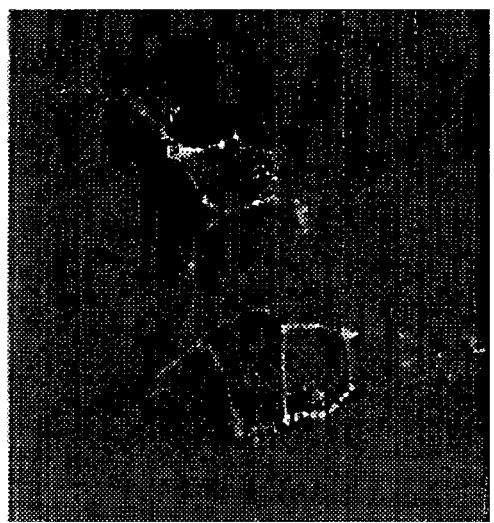
Figure 10B:
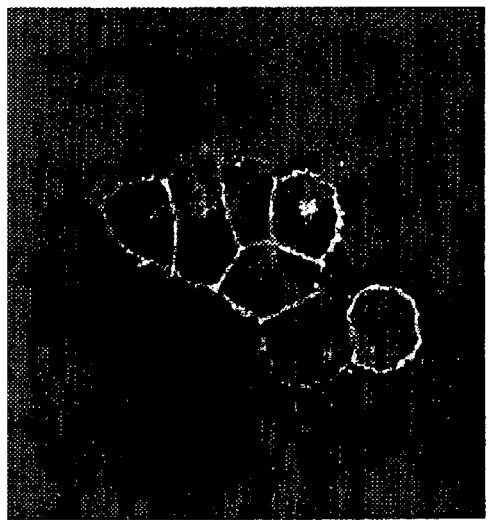
Figure 10B:
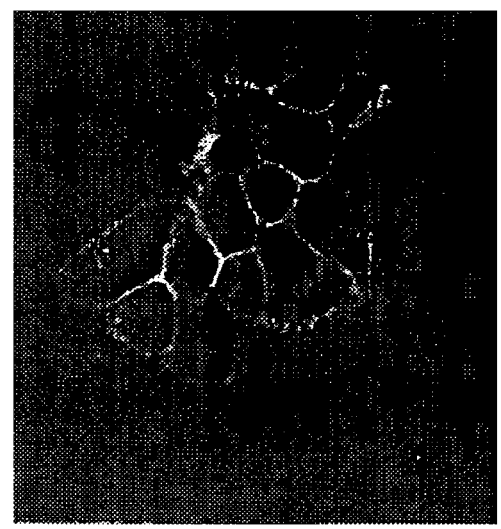
Figure 10B:
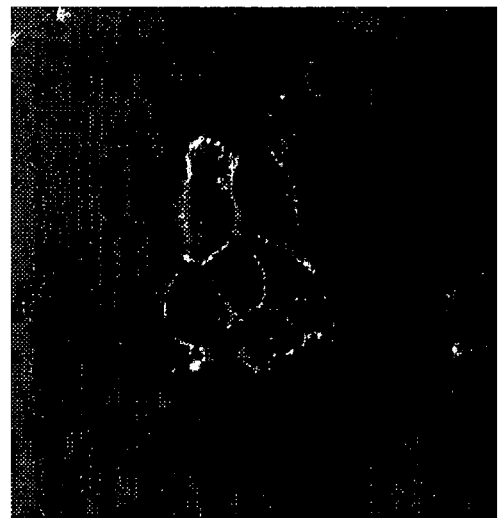
Figure 10C:
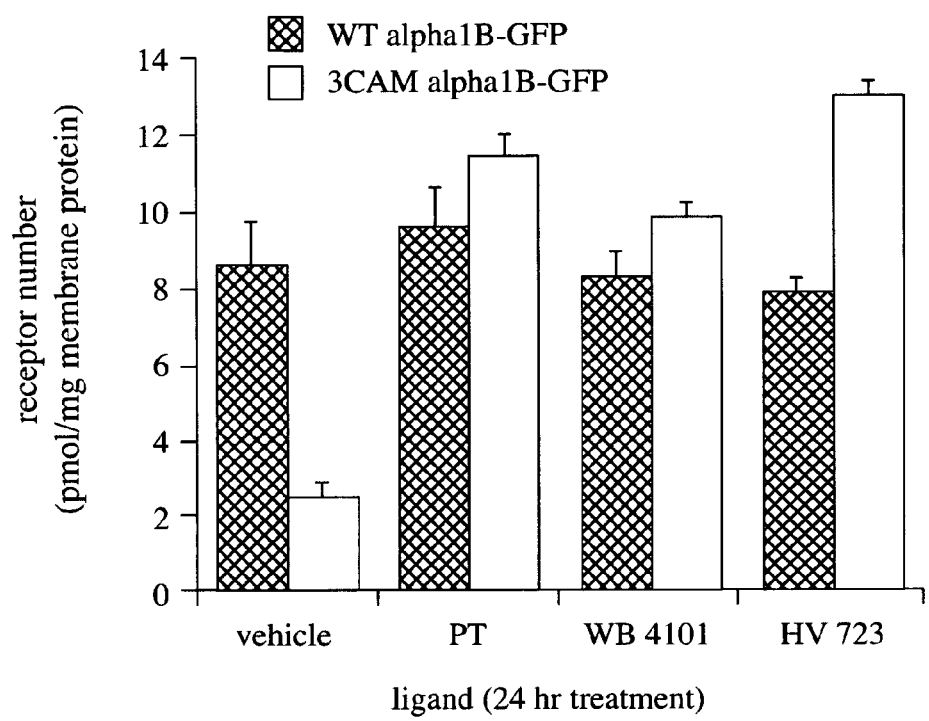

Equivalent studies were performed on plates of cells which were then washed and harvested. Membranes were prepared and the specific binding capacity of a single concentration (2 nM) of [$^3$H]prazosin was then assessed (FIG. 10C).

FIG. 11

Up-regulation of the WT and CAM $\alpha_{1b}$-adrenoceptor/GFP fusion protein following stable expression in HEK 293 cells. The graphs show the effect on total cellular fluorescence of 22 hour treatment with (A) phenylephrine, (B) phentolamine, (C) WB 4101 and (D) HV 723. In all graphs ▲ represents data obtained from wild type $\alpha_{1b}$-adrenoceptor/GFP and ● represents data from CAM $\alpha_{1b}$-adrenoceptor/GFP expressed in HEK 293 cells. All values are expressed as a percentage of the basal fluorescence and are the mean of at least 4 experiments performed in duplicate ±SEM.

FIG. 12

Time course of up-regulation of CAM $\alpha_{1b}$-adrenoceptor/GFP in NEK 293 cells. Graphs show the up-regulation of fluorescence caused with (A) phenylephrine, (B) WB 4101, (C) HV 723 and (D) phentolamine. The data represents one experiment performed in duplicate.

FIG. 13

Schematic diagram of the $\beta_2$-adrenergic receptor/luciferase fusion protein construct.

FIG. 14

Construction and conceptual use of a constitutively active β2-adrenoceptor linked to *Renilla reniformis* luciferase to identify antagonists at this receptor. The construct expressed in cells is treated with a ligand which binds to this receptor. This causes upregulation of the protein over time and thus higher levels of *Renilla reniformis* luciferase activity in the cell which can be monitored by standard procedures.

FIG. 15

Concentration-dependent increases in levels of a constitutively active β2-adrenoceptor linked to *Renilla reniformis* luciferase. Varying concentrations of 3 ligands which bind to the β2-adrenoceptor were added to wells of a 96 well microtitre plate containing cells which stably express a constitutively active β2-adrenoceptor linked to *Renilla reniformis* luciferase. These plates were then incubated for 24 hours after which time the media was pipetted off from each well.

50 ul of phenol red free media was then added to each well plus 50 ul of luc-lite solution (a commercial kit reagent which is optimised for *Renilla* luciferase activity and also contains a mild cell lysis component). Finally 50 ul of 15 uM coelenterazine in phenol red free media was added (to give a final concentration of 5 uM). The plates were then assayed immediately on a top count luminometer to determine the light intensity in relative light units.

FIG. 16

Laser scanning confocal images of HEX 293 cells stably transfected to express the PAR1mut/GFP fusion protein. Taken before (left hand image) and after 40 mins incubation with 10 μM TRAP (right hand image) A and B represent two different coverslips of cells.

FIG. 17

Agonist down-regulation of the PAR1mut/GFP fusion protein following stable expression in HEK 293 cells. The bar graphs show the effects of 4 hours treatment with either (A) TRAP or (B) thrombin. All values are expressed as a percentage of the basal fluorescence and are the mean of 2 experiments performed in quadruplicate.

MATERIALS AND METHODS I

[$^3$H]DHA (64 Ci/mmol) and [$^3$H]CGP-12177 (44 Ci/mmol) were purchased from (Amersham, UK). [$^3$H] adenine and [$^3$H]cAMP were purchased from Amersham International, Amersham, U.K. All reagents for cell culture were purchased from Life Technologies (Paisley, Strathclyde, U.K.). Receptor ligands were purchased RBI. All other reagents were purchased from Sigma or Fisons and were of the highest purity available.

Construction of GFP Tagged Forms of the $\beta_2$-adrenoceptor

Human wild type $\beta_2$-AR in pcDNA3 (MacEwan & Milligan 1996a) was amplified by PCR using a Hind III-FLAG forward primer, 5' AAAAAA AAGCTT GCCACC ATG GAC TAC AAG GAC GAC GAT GAT AAG GGG CAA CCC GGG AAC GGC 3', and a Bam HI reverse primer, 5' AAAAA GGATCC TCC CGC CAG CAG TGA GTC ATT TGT A 3'. This removed the stop codon and the initiating methionine (start codon) of $\beta_2$-WT-AR, with an initiator ATG being present in the N-terminally added FLAG™ epitope tag (ATG GAC TAC AAG GAC GAC GAT GAT AAG). The PCR product was digested with Hind III and Bam HI and the resulting fragment ligated into pcDNA3 to generate a wild type $B_2$-AR/GFP construct. Sequence encoding amino acids 172–291 of WT $B_2$ receptor were restricted this construct using Kpn I/Hpa I and replaced by the equivalent region of the CAM $β_2$-AR (Samama et al., 1993, 1994). A modified form of GFP (Zernicka-Goetz et al., 1997) was also amplified by PCR using a Bam HI forward primer, 5' AAAAA GGATCC AGT AAA GGA GAA GAA CTT TTC 3', and an Xba I reverse primer, 5' TGCTCTAGATTATTTGTATAGTTCATCCATGCC 3'. This removed the initiating methionine of GFP and the resulting PCR product was digested and linked in frame to generate the CAM $β_2$-AR-GFP construct.

Transient and Stable Transfection of HEK293 Cells

HEK293 cells were maintained in Minimum Essential Medium (MEM, Sigma) supplemented with 0.292 g/L L-glutamine, and 10% newborn calf serum at 37° C. in a 5% $CO_2$ humidified atmosphere. Cells were grown to 60–80% confluence prior to transient transfection. Transfection was performed using LipofectAMINE reagent (Life Technologies, Inc.) according to manufacturers' instructions. To generate stable cell lines, two days after transfection cells were seeded/diluted and maintained in MEM medium supplemented with 1 mg/ml Geneticin (Life Technologies, Inc.). Medium was replaced every 3 days with MEM medium containing 1 mg/ml Geneticin. Clonal expression was initially examined by fluorescence microscopy for the GFP containing clones. Selected clones expressing GFP and non-GFP tagged forms of the receptors were expanded and [$^3$H] ligand binding studies performed to assess the level of receptor expression.

Confocal Laser Scanning Microscopy

Cells were observed using a laser scanning confocal microscope (Zeiss Axiovert 100) using a Zeiss Plan-Apo 63×1.40 NA oil immersion objective, pinhole of 35, and electronic zoom 1 or 3. The GFP was exited using a 488 nm argon/krypton laser and detected with 515–540 nm band pass filter. The images were manipulated with Zeiss LSM or MetaMorph software. Two different protocols for preparation of cells were used. When examining the time course of internalisation and recycling live cells were used. Cells were grown on glass coverslips and mounted on the imaging chamber. Cells were maintained in KRH buffer (see below) and temperature was maintained at 37° C. In other studies fixed cells were used. Cells on glass coverslips were washed with PBS and fixed for 20 min at room temperature using 4% paraformaldehyde in PBS/5% sucrose pH 7.2. After one wash with PBS coverslips were mounted on microscope slides with 40% glycerol in PBS.

[$^3$H]Ligand Binding Studies

CAM $β^2$-AR-GFP cells were grown in 6 cm dishes and treated with or without 10 μM betaxolol or various concentrations of alprenlol for 24 h. In some cases betaxolol treated cells were subsequently exposed to 10 μM isoprenaline for 30 min. After treatment the cells were washed 3 times with ice cold phosphate-buffered saline (PBS; 2.7 mM KCl, 137 mM NaCl, 1.5 mM $KH_2PO_4$, 8 mM $Na_2HPO_4$, pH 7.4). Cells were then detached from plates with PBS/0.5 mM EDTA pelleted and resuspended in ice cold Krebs-Ringer-Hepes buffer (KRH; 130 mM NaCl, 5 mM KCl, 1.2 mM $MgSO_4$, 1.2 mM $CaCl_2$, 20 mM HEPES, 1.2 mM $Na_2PO_4$, 10 mM glucose, 0.1% BSA; pH 7.4) buffer. After counting the cells in a hemocytometer approximately 100,000 cells were added to each assay tube.

For binding studies a single concentration of [$^3$H] DHA (2 nM) or [$^3$H] CGP-12771 (10 nM) was used to measure total cell receptor and cell surface receptor respectively. Parallel studies with 10 μM propranolol allowed assessment of non-specific binding. [$^3$H] DHA binding assays were performed at 30° C. for 45 min and [$^3$H] CGP-12771 binding at 14° C. for 2.5 hours in KRH buffer. All experiments were terminated by rapid filtration through Whatman GF/C filters followed by three washes with ice-cold TE (75 mM Tris, 1 mM EDTA; pH 7.4) buffer.

Intact Cell Adenylyl Cyclase Activity Measurements

Were performed essentially as described by Wong (1994) and Mercouris et al. (1997). Cells were split into wells of a 12-well plate and the cells were allowed to reattach. Cells were then incubated in medium containing [$^3$H]adenine (1.5 μCi/well) for 16–24 h. The generation of [$^3$H]cAMP in response to treatment of the cells with various ligands and other reagents was then assessed. Results are presented as the ratio of levels of [$^3$H]cAMP to total [$^3$H]adenine nucleotides (×1000).

Immunoblotting Studies

Electrophoresis and Immunoblot Analysis

A borate-based electrophoretic buffer system[Poduslo, J. F. (1981) Anal. Biochem. 114, 131–139] was employed with some modifications. Briefly, the resolving polyacrylamide gel was made of 10% acrylamide, 0.0625% bisacrylamide, 0.1 M Tris (pH 8.5), 0.1 M boric acid, 0.0025 M EDTA, 0.1% SDS, 0.005% TEMED and 0.1% ammonium persulfate. The stacking gel was of the same composition except that it contained 4% acrylamide. The borate electrophoresis running buffer was composed of 0.1 M Tris, 0.1 M boric acid, 0.0025 M EDTA and 0.1% SDS (pH 8.5). Standard and borate electrophoresis were run for 1 h at 200 V and 150 V, respectively using a Mini Protean II gel kit (BIO-RAD, Hamel Hempstead, U.K.). After SDS-PAGE, proteins were electrophoretically transferred to nitrocellulose. The membrane was blocked for 1 h in 3% fat-free milk in PBS-T buffer (PBS containing 0.1% Tween 20). After a brief wash in PBS-T buffer, the membrane was incubated overnight at 4° C. with an appropriate primary antibody diluted in PBS-T buffer containing 1% fat-free milk. A GFP polyclonal antibody (Clontech Laboratories, U.K.) was used for the detection of the constructs. The primary antibody was then removed and the blot washed extensively in PBS-T buffer. Subsequent incubation with secondary antibody (donkey anti-rabbit IgG conjugated with horseradish peroxidase, Scottish Antibody Production Unit, Carluke Scotland) proceeded for 2 h at room temperature and after extensive washing in PBS-T buffer the blot was visualized by enhanced chemiluminescence ECL (Amersham). Quantitative analysis of specific bands was performed by scanning with an imaging densitometer GS-670 (BIORAD).

Studies in Microtitre Plates

Cells were seeded into black costar view plates the day before the experiment. On the day of the experiment the media was removed from the cells and drug added to the well in a final volume of 100 μl. The experiment was preformed in phenol red free F12 media containing 10% FCS. A Spectrafluor Plus fluorimeter was used to read the plates reading from the bottom at a gain of 100. A blank plate was initially read on the flourimeter and then the plates of cells were read at time 0 and after 22 hrs incubation at 37° C. with drug. Results were calculated by subtracting the blank plate from the fluorescence values obtained to control for plate autofluorescence.

EXAMPLE 1

Construction of GPCR/GFP Fusion Protein

A PCR based strategy was used to link a cDNA encoding a form of GFP with enhanced autofluorescence properties (Zernicka-Goetz et al., 1997) in-frame with cDNAs encoding both the wild type $\beta_2$-adrenoceptor and a constitutively active mutant form of this GPCR, produced by replacement of a small segment of the distal end of the third intracellular loop with the equivalent segment of the hamster $\alpha_{1B}$-adrenoceptor. These were anticipated to encode single open reading frames in which the C-terminus of the GPCR was linked directly to the N-terminus of GFP. Following transient transfection of these constructs and visualisation on a fluoresecence microscope to confirm successful expression and autofluorescence, both of these constructs and the equivalent non-GFP tagged forms of the GPCRs were expressed stably in HEK293 cells. Individual clones were identified based on a combination of appropriate autofluorescence and specific binding of the $\beta$-adrenoceptor antagonist [$^3$]dihydroalprenolol ([$^3$H] DHA) and subsequently expanded. In clones expressing the wild type $\beta_2$-adrenoceptor-GFP construct, confocal microscopy performed on intact cells grown on a glass cover slip demonstrated the bulk of the GFP-derived autofluorescence to be plasma membrane delineated (FIG. 1). Addition of the $\beta$-adrenoceptor agonist isoprenaline ($10^{-5}$ M) resulted in a time-dependent internalisation of the construct into discrete intracellular vesicles (FIG. 1) as has previously been reported for such a construct (Barak et al., 1997, Kallal et al., 1998). The wild type $\beta_2$-adrenoceptor-GFP construct internalised following 30 min treatment with isoprenaline and could be recycled to the plasma membrane following removal of isoprenaline and its replacement by the $\beta$-adrenoceptor antagonist alprenolol ($10^{-5}$M) (FIG. 2) which did not itself promote internalisation.

Although clones expressing the CAM $\beta_2$-adrenoceptor-GFP construct were also isolated these did not display the same level of GFP autofluoresence as the clones expressing the WT $\beta_2$-adrenoceptor-GFP construct. Such observations were consistent with routinely lower levels of steady state expression of the CAM $\beta_2$-adrenoceptor-GFP construct. This was confirmed by the lower levels of [$^3$H]DHA specific binding to membrane fractions isolated from these cells compared to clones expressing the wild type $\beta_2$-adrenoceptor-GFP construct. Furthermore, although clear plasma membrane-localised CAM $\beta_2$-adrenoceptor-GFP could be observed there appeared to be a greater fraction of the GFP autofluoresence located intracellularly than for the WT $\beta_2$-adrenoceptor-GFP (FIG. 3a).

EXAMPLE 2

Ligand Binding to GPCR/GFP Fusion Protein

The present applicants have previously postulated that sustained treatment of NG108-15 cells stably expressing the CAM $\beta_2$-adrenoceptor with the inverse agonist betaxolol can cause an increase in steady state levels of this GPCR. When cells expressing the CAM $\beta_2$-adrenoceptor-GFP construct were treated with betaxolol (24h, $10^{-5}$ M) and then visualised by confocal microscopy a marked increase in both plasma membrane delineated and intracellular fluoresence was observed (FIG. 3a). Washing of the cells followed by an intact cell ligand binding experiment with [$^3$H]DHA confirmed upregulation of CAM $\beta_2$-adrenoceptor-GFP in response to betaxolol (FIG. 3b). Upregulation of fluoresence was also observed by treatment of the cells with a range of $\beta_2$-adrenoceptor inverse agonist/antagonists including ICI118551, labetolol, carvedilol, alprenolol and dihydroalprenolol (all at $10^{-5}$ M) (FIG. 4). However, pharmacological selectivity of this effect was preserved as it was not recorded by treatment with the $\alpha_1$-adrenoceptor antagonist prazosin or the $\alpha_2$-adrenoceptor antagonist yohimbine (data not shown).

Sustained treatment of cells expressing wild type $\beta_2$-adrenoceptor-GFP with betaxolol or the other ligands described above failed to result in a significant upregulation of the construct as fluorescence intensity and distribution pattern was little modified by the drug treatments (data not shown). Upregulation of CAM $\beta_2$-adrenoceptor-GFP by betaxolol treatment could also be monitored in immunoblot experiments to confirm the effects seen by confocal microscopy. Membranes isolated from either wild type $\beta_2$-adrenoceptor-GFP or the CAM $\beta_2$-adrenoceptor-GFP expressing cells following maintenance in the presence or absence of betaxolol ($10^{-5}$ M) for 24h were resolved by SDS-PAGE and the GPCR constructs detected by immunoblotting with an anti-GFP antibody. Clear upregulation of CAM $\beta_2$-adrenoceptor-GFP but not wild type $\beta_2$-adrenoceptor-GFP was observed (FIG. 5).

Figure 6B:
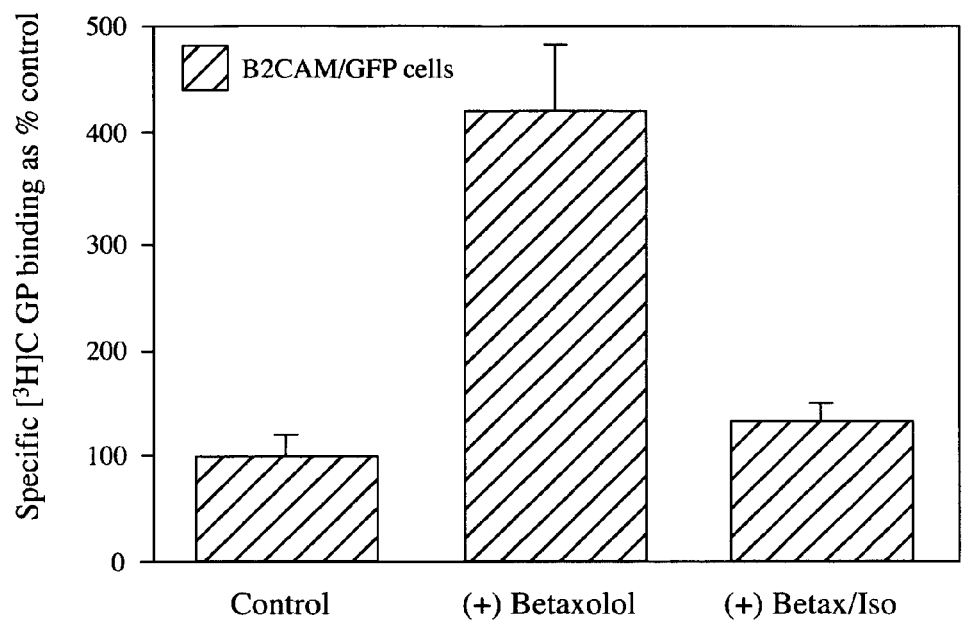

Following betaxolol-induced upregulation of CAM $\beta_2$-adrenoceptor-GFP removal of this ligand, and its replacement by isoprenaline ($10^{-5}$ M), resulted in a rapid internalisation of the construct into intracellular punctate vesicles in a manner which was indistinguishable from that recorded above for wild type $\beta_2$-adrenoceptor-GFP (FIG. 6a). [$^3$H] CGP-12177 is a hydrophillic $\beta_2$-adrenoceptor antagonist which is unable to cross the plasma membrane. Therefore in intact cell specific binding experiments it identifies only the cell surface population of the $\beta_2$-adrenoceptor. Such intact cell binding studies were performed on cells expressing CAM $\beta_2$-adrenoceptor-GFP, cells which had been pretreated with betaxolol (24h, $10^{-5}$ M), and such cells after replacement of betaxolol with isoprenaline ($10^{-5}$ M) for 30 min. These studies demonstrated that cell surface upregulated CAM $\beta_2$-adrenoceptor-GFP was largely internalised by agonist treatment (FIG. 6b).

Upregulation of CAM $\beta_2$-adrenoceptor-GFP by sustained treatment with betaxolol and $\beta$-adrenoceptor antagonist/inverse agonist ligands could be detected and directly quantitated in a Spectrofluor Plus fluorimeter following seeding of cells into a 96 well microtitre plate. This allowed analysis of the concentration-dependence of CAM $\beta_2$-adrenoceptor-GFP upregulation with various inverse agoinst/antagonists after 22 h incubation with the compounds (FIG. 7a). Betaxolol gave the clearest response (FIG. 7b) producing an upregulation of the construct with an $EC_{50}$ of 168(47–600) nM, a value in good accordance with the measured $K_1$ of betaxolol to bind to this GPCR construct (MacEwan & Milligan 1996a). Treatment of the WT $\beta_2$-adrenoceptor-GFP fusion with betaxalol did not result in any change in cellular fluorescence following either 1 h or 22 h of drug incubation. However, incubation of such cells with the agonist ligand isoprenaline for 22h resulted in a marked reduction of cellular fluorescence which upon quantification in the Spectrofluor Plus fluorimeter allowed an analysis of the concentration dependence of isoprenaline mediated changes in cellular fluorescence. Isoprenaline caused a decrease in cellular fluorescence an IC50 of 13(2.5–70) nM (FIG. 7c). This contrasts with a reported $EC_{50}$ of 5 nM for the stimulation of cAMP by this drug at this receptor.

In summary this example shows that inverse agonist or neutral antagonist treatment of cells expressing a CAM $\beta_2$-adrenoceptor-GFP fusion construct results in an increase in membrane fluorescence as detected by confocal microscopy, and an increase in total cellular fluorescence as measured by microplate fluorimetry. The concentration dependence of these effects agrees with data obtained from traditional pharmacological studies thus validating the use of this approach for the characterisation of compounds which effect receptor function. The ability of inverse agonist or antagonist ligands to cause an increase in cellular fluorescence from cells expressing a CAM GPCR-GFP fusion allows for the provision of a microplate based fluorescence assay for new compounds with similar activity.

Agonist treatment of cells expressing the WT $\beta_2$-adrenoceptor-GFP fusion was observed to result in a decrease in membrane associated fluorescence and an increase in fluorescence in intracellular vesicles which by co-immunolocalisation studies with an anti-transferrin antiserum are shown to be endosomes. The decrease in fluorescence observed by micrioplate fluorimetry following internalisation of the fusion protein may be due in part to receptor degradation but may also be due to a fluorescence quenching event as a consequence of receptor concentration within the acidic environment of the endosome compartment. However, this decrease in fluorescence caused by agonist ligands such as isoprenaline is concentration dependent and the half maximal drug concentrations required to cause this effect is in agreement with the values obtained in traditional second messenger analysis studies.

Thus the example discloses a novel screening system for compounds with either agonist, neutral antagonist or inverse agonist activity at the $\beta_2$-adrenoceptor in which compound activity results in a change in the fluorescence characteristics of cells expressing a β2-adrenoceptor-GFP fusion protein. The change in the fluorescence characteristics can be measured by either a change in cellular localisation using the confocal microscope, or by a change in total cellular fluorescence as measured in a 96-place fluorimeter. Using confocal microscopy as the detection system, an antagonist/inverse ligand would cause an increase in cell surface fluorescence of the CAM GPCR/GFP fusion protein while an agonist ligand would cause an increase in internalization of a WT GPCR/GFP fusion protein.

MATERIALS AND METHODS II

Construction of GFP-Tagged Forms of the 3CAM$\alpha_{1B}$-adrenoceptor.

Production and subcloning C-terminally GFP tagged forms of wild type and 3CAM (R288K, K290H, A293L) forms of the hamster $\alpha_{1B}$-adrenoceptor was performed in two separate stages. In the first step the coding sequence of a modified form of GFP was modified by polymerase chain reaction (PCR) amplification. Using the amino-terminal primer 5'-GGAA GGTACCAGTAAAGGAGAAGAACTT-3 the initiating Met of GFP was removed and both a Kpn I restriction site (underlined) and a 2-amino acid spacer (Gly-Asn) were introduced. Using the carboxy-terminal primer 5-TGC TCTAGATTATTTGTATAGTTCATCCATGCCATG-3' an Xba I restriction site (underlined) was introduced downstream of the stop codon of GFP. The amplified fragment of GFP digested with Kpn I and Xba I was subcloned into similarly digested pcDNA3 expression vector (Invitrogen).

To obtain the $\alpha_{1B}$-adrenoceptor-GFP fusion proteins, the coding sequence of each form of the $\alpha_{1B}$-adrenoceptor was amplified by PCR. Using the amino-terminal primer 5'-GAC GGTACCTCTAAAATGAATCCCGAT-3', a Kpn I restriction site (underlined) was introduced upstream of the initiator Met. Using the carboxy-terminal primer 5'-GTCCCT GGTACCAAAGTGCCCGGGTG-3', a Kpn I restriction site (underlined) was introduced immediately upstream of the stop codon. Finally, the GFP construct in pcDNA3 was digested with Kpn I and ligated together with the PCR product of the $\alpha_{1B}$-adrenoceptor amplification also digested with Kpn I. The open reading frames so produced represent the coding sequence of either the wild type or 3CAM $\alpha_{1B}$-adrenoceptor-GFPs. Each was fully sequenced prior to its expression and analysis.

Transient and Stable Transfection of HEK293 Cells.
As previously described in Material and Methods I.

Preparation of membranes.
HEK293 cells stably expressing each of the $\alpha_{1B}$-adrenoceptor-GFP fusion proteins were grown to confluence on 6 cm dishes. Prior to harvesting, cells were washed twice with 4 ml of ice-cold TE buffer (10 mM Tris, 0.1 mM EDTA pH 7.5) and then scraped into 1 ml of the same buffer. Rupture of the cells was achieved with 25 strokes of a hand-held glass Dounce homogenizer on ice. The suspension was centrifuged at 16000×g for 15 min and the resulting pellets resuspended in ice-cold TE buffer to final protein concentrations of 0.035–0.16 mg/ml.

[$^3$H]Prazosin-binding experiments.
Binding experiments were initiated by the addition of 0.7–3.2 µg of membrane protein to an assay buffer (75 mM Tris/HCl (pH 7.5), 5 mM EDTA, 12.5 mM MgCl2 (buffer A) containing [$^3$H]prazosin (2 nM). Non-specific binding was determined in the presence of 10 µM phentolamine. Reactions were incubated for 30 min at 30° C. and bound ligand was separated from free ligand by vacuum filtration through GF/B filters. The filters were washed twice with buffer A and bound ligand was estimated by liquid-scintillation spectrometry. Specific binding is displayed Confocal Laser Scanning Microscopy
As previously described in Materials and Methods I.

EXAMPLE 3

Upregulation of the 3CAM but not Wild Type Hamster $\alpha_{1b}$-adrenoceptor by Sustained Antagonist/Inverse Agonist Challenge Constructs encoding GFP protein linked in-frame with both wild type and 3CAM forms of the hamster $\alpha_{1b}$-adrenoceptor were prepared as above (Materials and Methods II).

Figure 9:
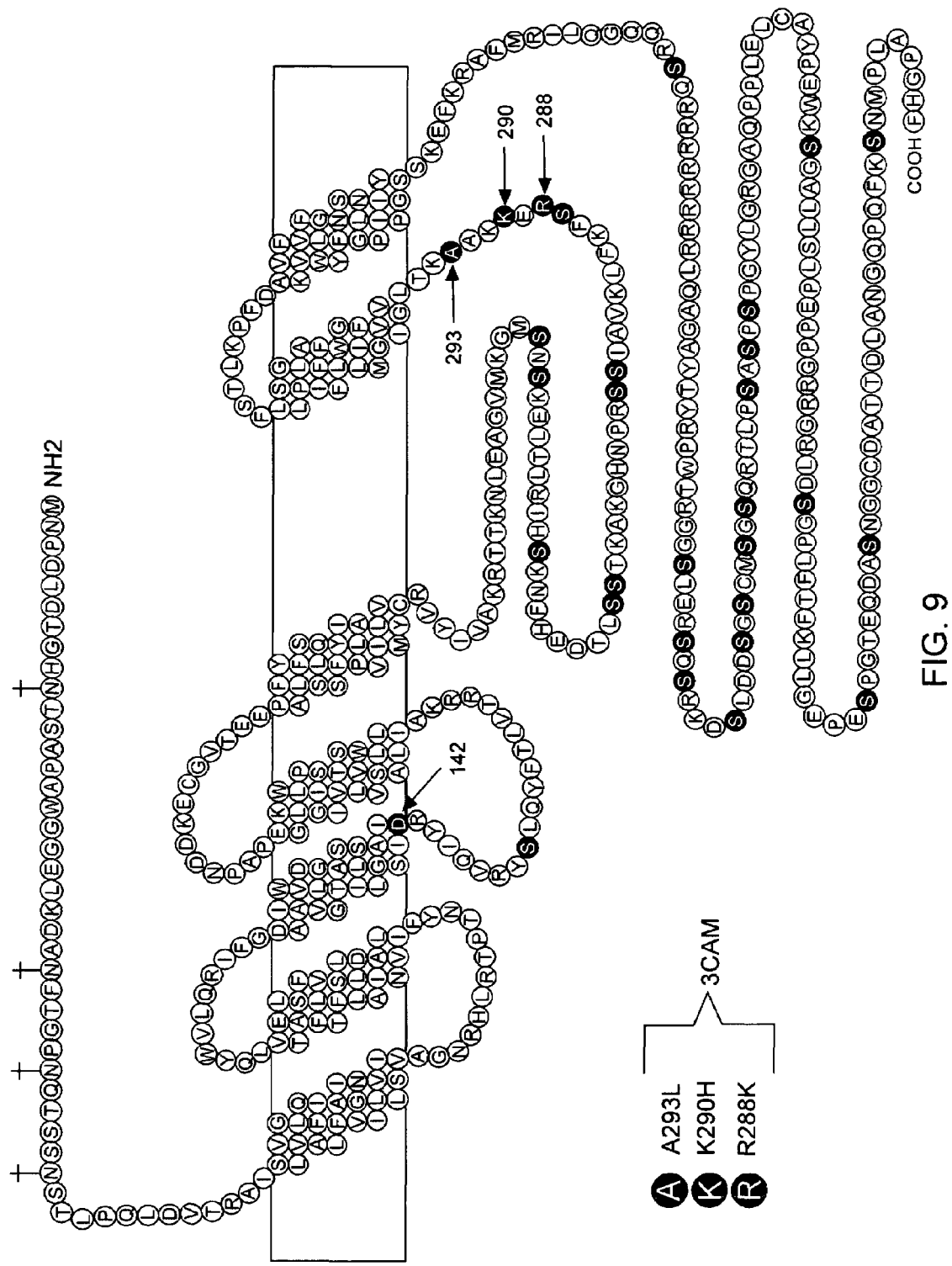

A more detailed description of the mutations in the wild type $\alpha_{1b}$-adrenoceptor primary amino acid sequence that give rise to the various forms (R288K, K290H, A293L) of constitutively active mutant (CAM) $\alpha_{1b}$-adrenoceptor is shown in FIG. 9. Such constructs were used to transfect HEK293 cells followed by selection of transfected cells expressing either the 3CAM or wild type $\alpha_{1b}$-adrenoceptor as before (Materials and Methods I—transient and stable transfection of HEK293 cells). Such cells were used in [$^3$H] ligand binding studies to assess the level of receptor expression. Upregulation of fluoresence was observed on treatment of cells expressing the 3CAM $\alpha_{1b}$-adrenoceptor/GFP fusion construct with a range of $\alpha_{1b}$-adrenoceptor inverse agonist/ antagonists (FIG. 10A (b)–(d)). However, treatment of cells expressing wild type $\alpha_{1b}$-adrenoceptor/GFP fusion construct with the same ligands, as for 3CAM above, failed to result in any significant upregulation of the construct, as fluorescence intensity and distribution pattern was little modified by the drug treatments (FIG. 10B (b)–(d)) compared with vehicle treatments only (FIG. 10B (a)).

Equivalent studies on both 3CAM and wild type $\alpha_{1b}$-adrenoceptor with the $\alpha_{1b}$-adrenoceptor antagonist prazosin are shown in FIG. 10C. It can be seen that prazosin (PT) has no effect on the wild-type $\alpha_{1b}$-adrenoceptor whereas it has the effect of upregulation of the mutant 3CAM form.

EXAMPLE 4

Ligand Up-regulation of CAM $\alpha_{1b}$-adrenoceptor/ GP Fusion Protein in HEK 293 Cells Methods HEK 293 cells stably expressing the wild type $\alpha_{1b}$-adrenoceptor/GFP construct or the constitutively active mutant (CAM) $\alpha_{1b}$-adrenoceptor/GFP fusion protein were produced as described previously in Materials and Methods II. These cell lines were used to investigate ligand up-regulation of the CAM $\alpha_{1b}$-adrenoceptor/GFP fusion protein. Fusion protein upregulation was measured according to a gain in total cellular fluorescence in a plate based fluorimeter.

Cells were maintained in Dulbecco's Modified Eagle's Medium (DMEM) supplemented with 10% v/v foetal calf serum (FCS), 2 mM L-glutamine and 1 mg/ml geneticin (growth media; all reagents from Life Technologies) at 37° C. in 5% $CO_2$ and 95% humidity. For experiments cells were seeded into black 96 well view plates (Costar) on the day before assay. On the day of assay the growth media was removed and replaced with phenol red free DMEM/F12 (1:1) medium containing 5% v/v FCS, 2 mM L-glutamine in the presence of various concentrations of test compounds (phenylephrine, phentolamine, WB4101 and HV723) in a final volume 100 µl. Cells were incubated at 37° C. for 22 hours. After incubation fluorescence was detected using a Tecan Spectrafluor plus fluorimeter. To control for plate and media autofluorescence results were calculated by subtracting a blank plate reading from the fluorescence values obtained in drug treated cells.

Results

Figure 11:
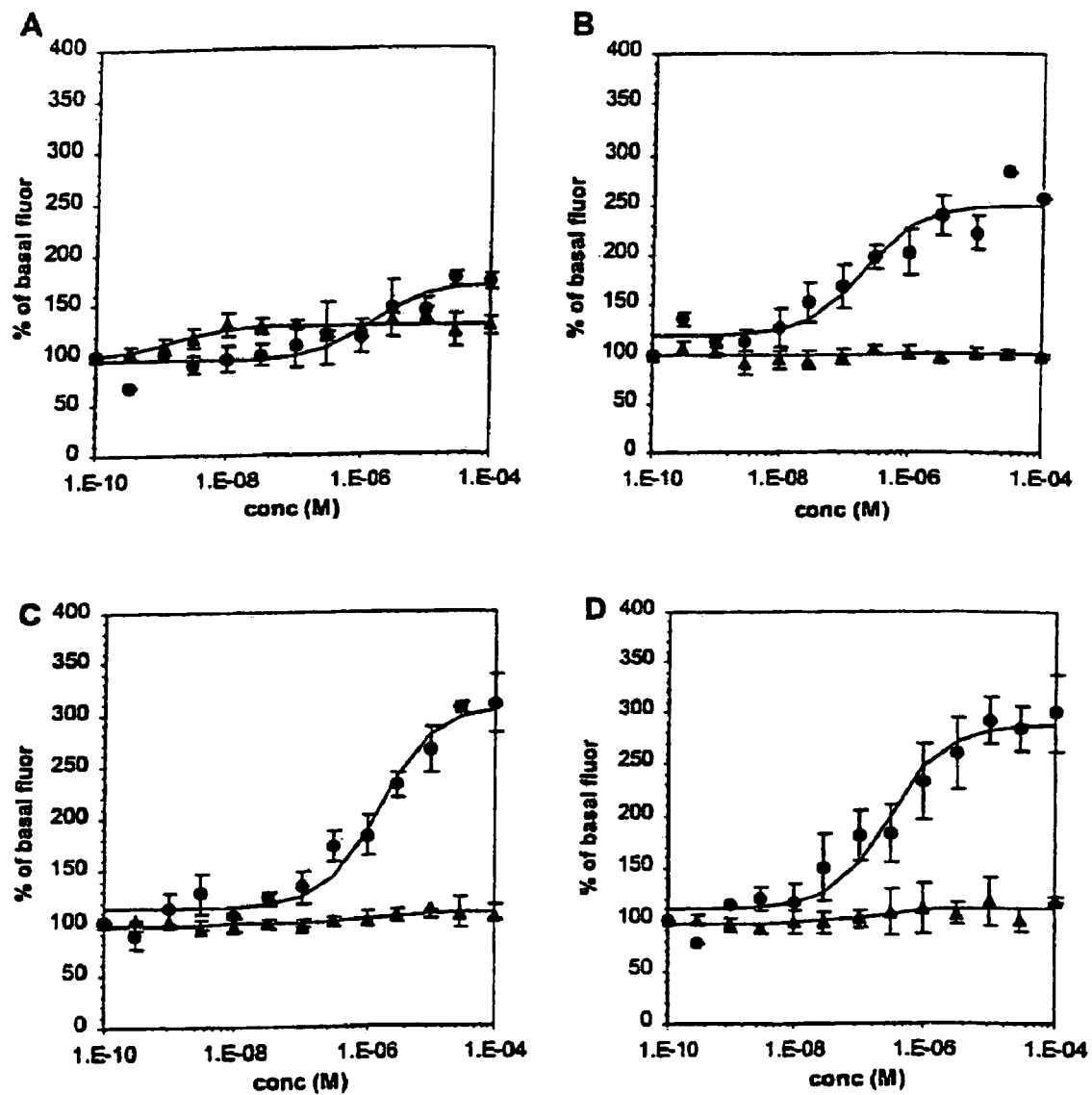

HEK 293 cells stably expressing either the wild type $\alpha_{1b}$-adrenoceptor/GFP fusion protein or the CAM $\alpha_{1b}$-adrenoceptor/GFP were treated with a range of compounds to examine ligand stabilisation of fusion protein expression. Four compounds were chosen for this experiment, the agonist phenylephrine and three compounds previously shown to display inverse agonist activity at this receptor; WB 4101, HV723 and phentolamine. The level of fusion protein expression was determined by detecting changes in GFP expression by plate fluorimetry. All compounds tested had no effect on the expression level of the wild type $\alpha_{1b}$-adrenoceptor/GFP fusion protein (FIG. 11). However long term treatment (22 hrs) of cells expressing the CAM $\alpha_{1b}$-adrenoceptor/GFP fusion protein with these compounds caused a dose dependant up-regulation of fluorescence (FIG. 11) with $EC_{50}$ values of 407(15–10471)nM for phenylephrine, 676(195–2344)nM for WB 4101, 417(71–2455)nM for HV 723 and 170(32–891)nM for phentolamine.

EXAMPLE 5

Time Course of up-regulation of CAM $\alpha_{1b}$-adrenoceptor/GFP Fusion Protein in HEK 293 Cells Methods The time course of ligand up-regulation of the CAM $\alpha_{1b}$-adrenoceptor/GFP fusion protein was also investigated. In this study cells were seeded and treated with drug as previously described but fluorescence in the blank plate and the cell plates were read at various time points between 2–31 hours after drug addition.

Results

Figure 12:
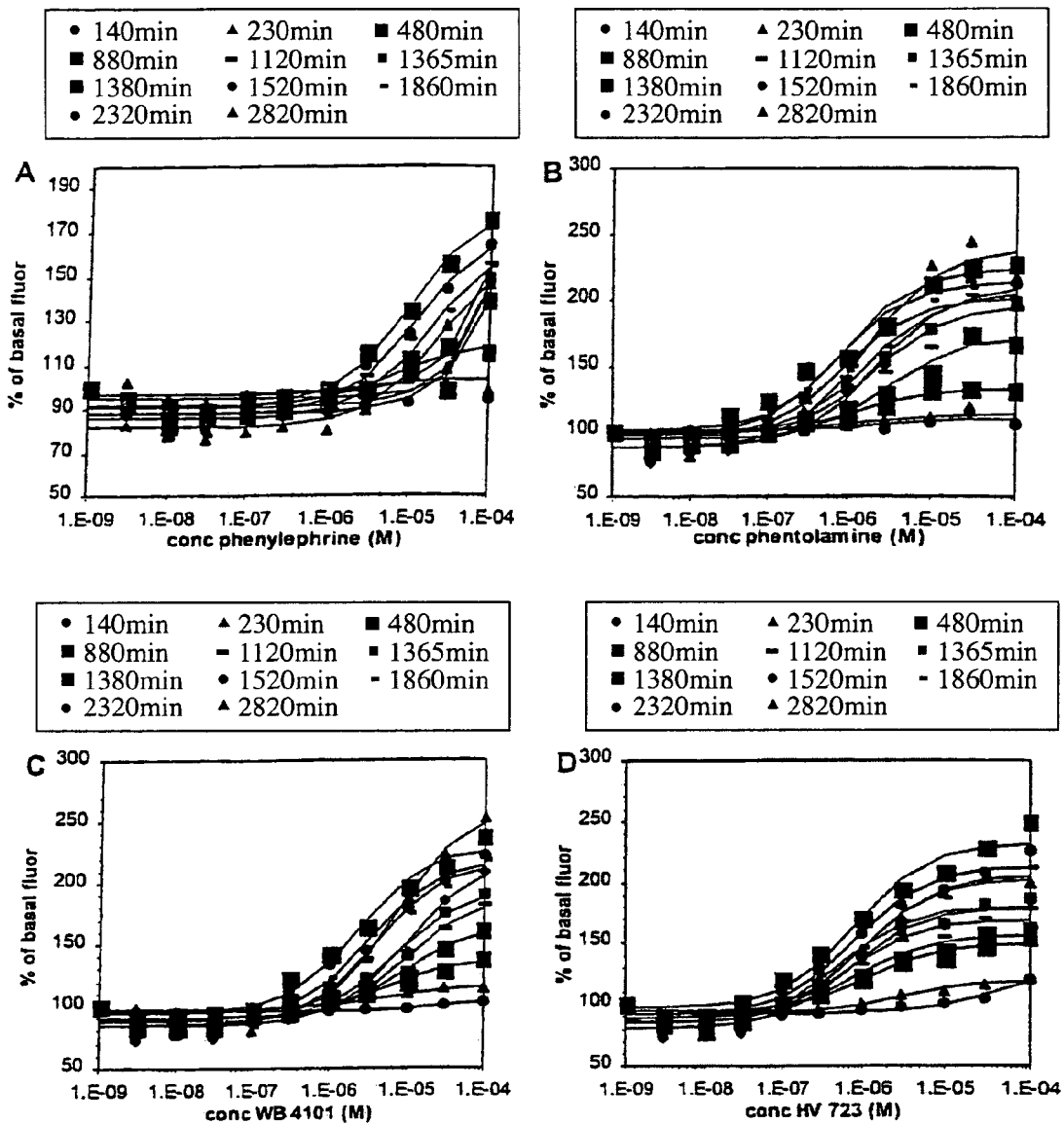

For all compounds tested there was a gradual increase in fluorescence over time. At all time points the $EC_{50}$ for this dose related effect were unchanged (FIG. 12). The magnitude of the response reached a maximum after about 23 hrs incubation with the compounds. After this time the response remained relatively constant.

MATERIALS AND METHODS III

Construction of $\beta_2$-adrenergic Receptor/Luciferase Fusion Proteins

Both β2-AR/RLuc and β2-AR/RLuc(CAM) were generated as follows. A β2-AR fragment was generated via PCR amplification of an existing β2-AR gene which had been cloned into pcDNA3, generation of the β2-AR(CAM) fragment was also via PCR amplification of a mutated version of β2-AR cloned into pcDNA3 plasmid vector. The mutations consisted of 4 amino acid substitutions in intracellular loop 3 of the seven transmembrane domain receptor. As these were the only differences between the two versions of β2-AR, the primers which were generated for the PCR procedure could be used to generate both the β2-AR and it's CAM counterpart. The primers were as follows: 5' end forward primer 5'-AAA AAG CTT GCC ACC ATG GGG CAA CCC GGG AA-3' which incorporates both a 5' HINDIII cloning site and Kozac sequence. The 3' end reverse primer had sequence 5'-CCT CTC GAG CAG TGA GTC ATT-3' which incorporates an XhoI cloning site to allow linkage to the *renilla* luciferase gene. Introducing the Xho1 site results in an insertion of a glutamate residue in between the β2-AR gene and the *Renilla* luciferase. It also resulted in altering the last nucleotide in the amino acid coding sequence of β2-AR (G--->C), but this did not alter the amino acid sequence since the new codon CTC still encodes a leucine residue.

*Renilla* luciferase was similarly generated via PCR amplification of a *renilla* luciferase gene cloned into a plasmid vector called pRLCMV(from promega). The primers used for amplification were as follows: 5' end forward primer 5'-TCG CTC GAG ACT TCG AAA GTT TAT G-3' which incorporates an Xho1 site at the 5' end of the gene to allow linkage to either the β2-AR or the β2-AR(CAM) fragment. The reverse primer had the following sequence 5'-GCG TCT AGA TTA TTG TTC ATT TT-3' which incorporates both an Xba1 site into the 3' end of the gene immediately downstream of the stop codon.

Once the PCR reactions had been performed the resultant fragments were digested with the appropriate enzymes and subsequently gel purified, pcDNA3 plasmid vector was also digested with HindIII and XbaI to provide a recipient vector for the ligated fragments. Ligations were performed using a commercial DNA ligation kit (Fast-link DNA ligation kit from CAMBIO) in which digested pcDNA3, β2-AR (or β2-AR(CAM) fragment and *Renilla* luciferase fragment were mixed and ligated together. This was done sequentially, ligating the PCR fragments together first and then adding the digested vector, to yield the desired constructs which are diagramatically represented on FIG. 13.

Protocol for Measuring Drug Mediated Upregulation of (CAM)β2-AR/Rluc (Bioluminescence Assay)

A stably transfected cell line of HEK293 cells expressing the constitutively active (CAM)β2-adrenoceptor linked to luciferase from the sea pansy *Renilla reniformis*. was used to seed 96 well microtitre plates. The 96 well plate was then incubated overnight and on the following day the cells were about 80% confluent. Drug dilutions were then prepared: isoprenaline, betaxalol, sotalol and ICI118 551 were all freshly weighed out on the day of the experiment, whereas propranalol, salmeterol and salbutamol were prepared using 10e-2 preweighed stocks (dissolved in DMSO). Stock solutions for the 10 point curve were then prepared using either 10e-2 or 10e-3 as the top concentration point depending on the type of drug used, such dilution's were carried out in phenol red free media.

10 ul from each of the 10 point stock solutions were then added to wells of the 96 well plate diluting the drug 1 in 10 so that the highest final concentration of the drug was either 10e-3 or 10e-4 depending on the type used. These plates were then incubated for 24 hours after which time the media was pipetted off from each well.

50 ul of phenol red free media was then added to each well plus 50 ul of luc-lite solution (a commercial kit reagent which is optimised for *Renilla* luciferase activity and also contains a mild cell lysis component). Finally 50 ul of 15 uM coelenterazine in phenol red free media was added (to give a final concentration of 5 uM). The plates were then assayed immediately on a top count luminometer to determine the light intensity in relative light units.

EXAMPLE 6

Analysis of Ligand Induced Regulation in Cellular Levels of Constitutively Active Mutant Forms of β$_2$-adrenoceptor Linked to Luciferase from the sea pansy *Renilla reniformis*

Figure 13:
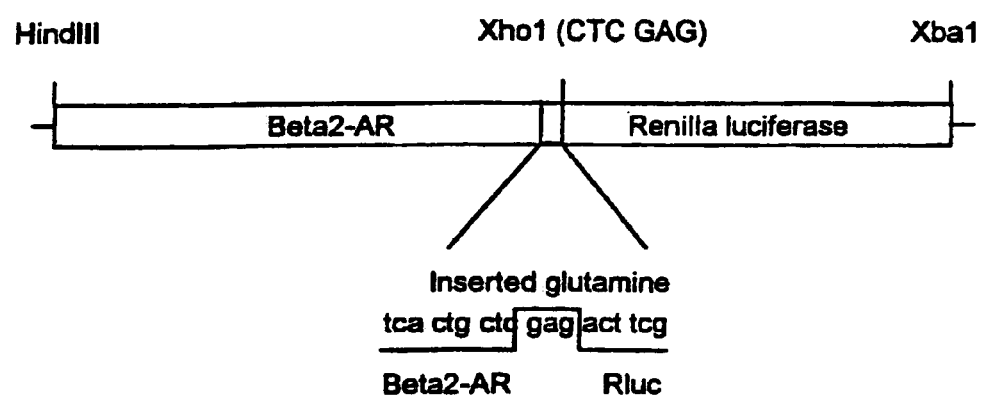
Figure 13:
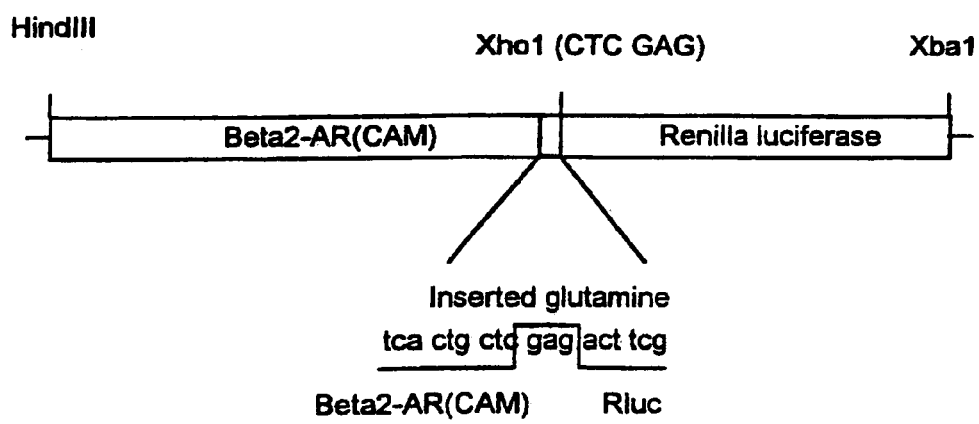
Figure 14:
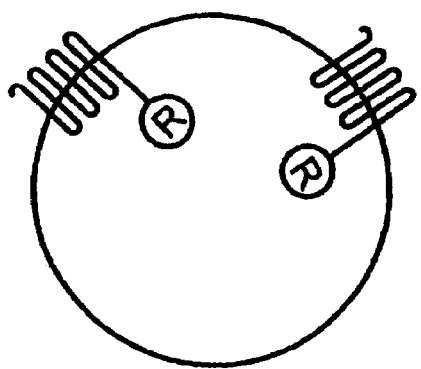
Figure 14:
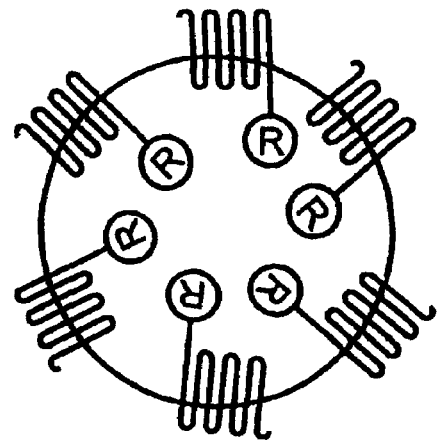
Figure 15:
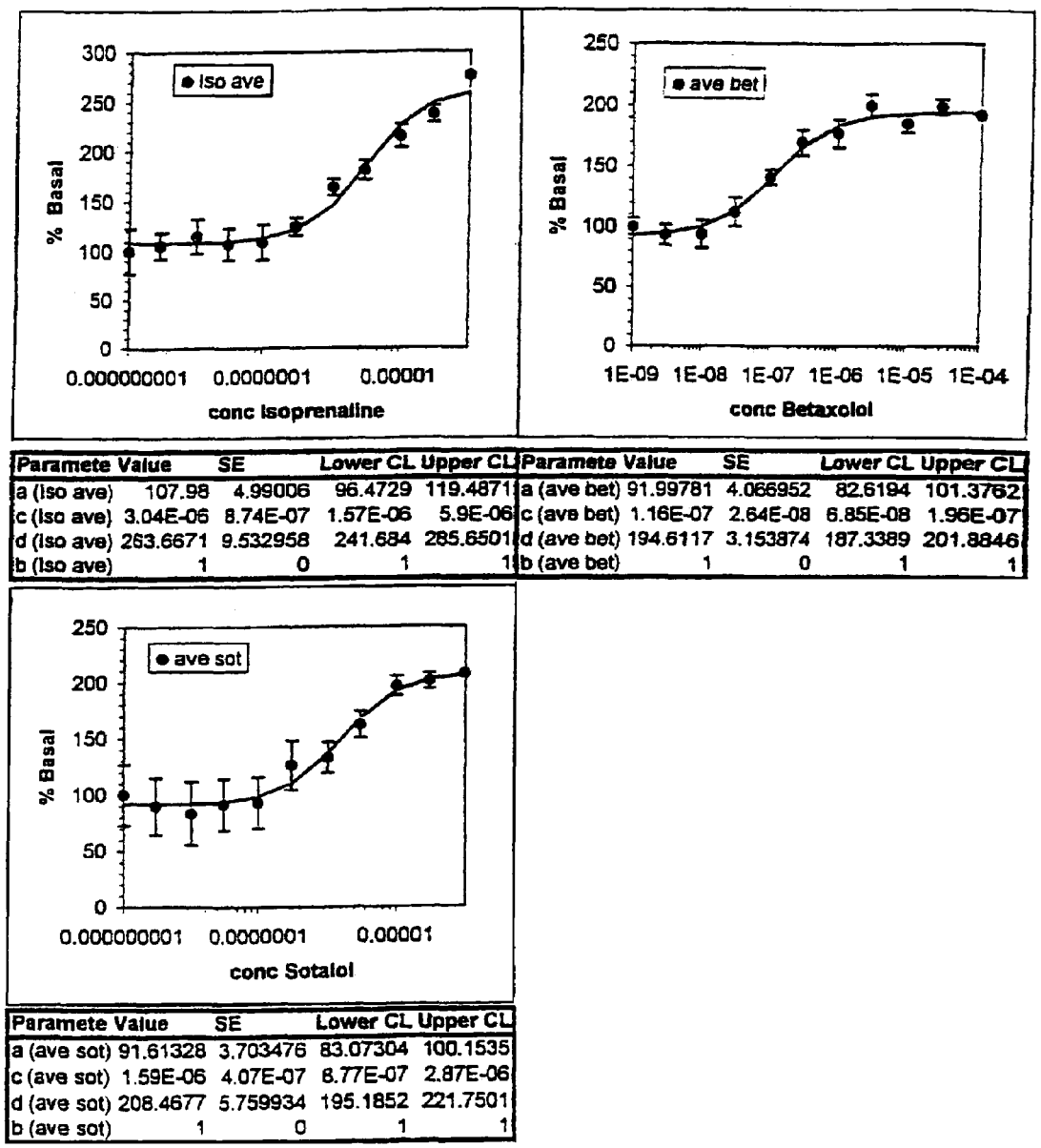

Constructs of a mutant (CAM) form of the β$_2$-adrenergic receptor (β$_2$-AR) linked to the *Renilla reniformis* luciferase protein were constructed as previously described (Materials and Methods III; FIG. 13). Such constructs were used to transfect HEK293 cells, with transfected cells expressing the desired proteins selected for further use. Selected cells were treated with various ligands as described above (Materials and Methods III—protocol for measuring drug medicated upregulation of (CAM) β$_2$-adrenergic receptor/*Renilla reniformis* luciferase fusion constructs). FIG. 14 shows a schematic diagram of the upregulation of CAM β$_2$-adrenoceptor in cells treated with a ligand that binds to this receptor. FIG. 15 displays results obtained on treatment of cells expressing CAM β$_2$-adrenoceptor/*Renilla reniformis* luciferase fusion constructs with ligands. It can be seen that the ligands Isoprenaline, Betaxolol and Sotalol upregulate the expression of the CAM-β$_2$-adrenoceptor in a concentration-dependent manner.

MATERIALS AND METHODS IV

Construction of a Mutated PAR1 Receptor Fused to GFP

A fusion protein was generated between a mutant of human PAR1 (Protease Activated Receptor 1) and GFP. PAR1 receptor internalisation occurs through two mechanisms. The receptor constitutively internalises and is recycled to the cell membrane in the absence of ligand. Following thrombin cleavage, and receptor activation, the receptor is internalised and targeted for lysosomal degradation (Shapiro, M J and Coughlin, S R. J. Biol. Chem 273, 29009–29014, 1998). The mutant PAR1 receptor used in this study contains a specific mutation within the intracellular C-terminal tail of the receptor that abolishes constitutive receptor internalisation and recycling to the membrane. This mutation replaces amino acid residues 397–406 in the wild type receptor with the sequence AlaGlyAlaGlyAlaGlyAla-GlyGlyAla (Shapiro and Coughlin, 1998). Hence following thrombin cleavage the mutant PAR1/GFP fusion protein will be targeted to the lysosome to cause a decrease in cell fluorescence.

The human PAR1 receptor was previously cloned corresponding to Genbank M62424 (Vu, T. et al., (1991) Cell 64, 1057–1068). As a first step in the construction of the PAR1/GFP fusion the receptor was PCR amplified using a sense primer NB100 and antisense primer, NB101 containing a BamHI restriction site (Table 1; underlined). During PCR the stop codon is removed and a BamHI site is introduced at the 3'end of the PAR1 open reading frame. The PCR product was ligated into pCR Blunt according to the manufacturers instructions (Invitogen) to generate pCR/PAR1-BamHI and the sequence verified. This plasmid was digested using restriction endonucleases EcoR1 and BamH1 to release the receptor sequence which was then ligated into similarly digested pEGFP-N1 (Clontech) to generate a WT PAR1/GFP fusion protein (plasmid designated pPAR1/GFP).

In order to replace amino-acid residues 397 to 406 of the PAR1 receptor with the sequence AlaGlyAlaGlyAlaGlyAla-GlyGlyAla two PCR reactions were performed using the WT PAR1 receptor in pCR/PAR1-BamHI as the PCR template. The sense primer NB102 (Table 1), corresponding to nucleotide residues 504–526 of the human PAR1 open reading frame immediately 5' to a PstI restriction site used in later cloning steps, and the antisense primer NB103, corresponding to nucleotides 1167 to 1187 containing a 13 nucleotide tail encoding amino acids AlaGlyAlaGly (bold in Table 1), were used in the first PCR. The second PCR used the sense PCR primer NB104 (Table 1), corresponding to nucleotide residues 1217–1241 of the human PAR1 open reading frame containing an additional 17 nucleotide 3' tail encoding amino acids AlaGlyAlaGlyGlyAla (bold in Table 1) and the antisense primer NB105. Prior to PCR primers NB103 and 104 were 3' phosphorylated using T4 polynucleotide kinase. Following PCR amplification, the two PCR products were ligated together. The DNA fragment generated as result of the ligation was used as template in a further PCR reaction using primers NB102 and NB101 to introduce a BamHI site at the 3' end of the PAR1 open reading frame as before. The PCR product was cloned into pCR Blunt (Stratagene). This fragment was sequenced to check that the mutation-had been successfully introduced.

The mutated fragment was excised from pCR/Blunt following digestion with restriction enzymes PstI and BamHI and subcloned into similarly digested pPAR1/GFP to generate pPAR1/mut/GFP. PAR1mutGFP was then excised from pPAR1/mut/GFP following digestion with restriction enzymes EcoRI and NotI and subcloned into similarly digested pCIN for stable mammalian expression (Rees, S., et al., Biotechniques 20, 102–110; 1996).

Stable Cell Line Construction

CHO (Chinese Hamster Ovary) cells were transfected with pCIN/PAR1mut/GFP using the Lipofectamine reagent (Life Technologies) according to the manufacturer's instructions. Transfected cells were selected in DMEM/F12 (1:1) media containing 5% v/v FCS, 2 mM L-glutamine and 1 mg/ml geneticin (all reagents from Life Technologies). After 2 weeks cells were dilution cloned to identify single clonal isolates. Clonal isolates were expanded over passage and clones expressing the PAR1/GFP fusion protein were identified by examining fluorescence intensity by Fluorescence Activated Cell Sorting (FACS).

Confocal Imaging of Agonist Mediated Internalisation of the PAR1mut/GFP Fusion Protein Cells were grown on 24 mm coverslips in extracellular media (125 mM NaCl, 5 mM KCl, 1.8 mM $CaCl_2$, 2 mM $MgCl_2$, 0.5 mM $NaH_2PO_4$, 5 mM $NaHCO_3$, 10 mM HEPES, 10 mM glucose, 0.1% BSA, pH 7.4). The coverslip was mounted in the imaging chamber of a Lecia TCS NT laser scanning confocal microscope (Lecia UK Ltd). Cells were observed with a 63×NA1.2 Plan Apo water immersion objective lens. GFP was excited using a 488 nm argon/krypton laser fluorescence emission was detected with a 525+/−25 bandpass filter. An image was recorded before and 40 min after the addition of the PAR1 agonist ligand TRAP (10 μM). Images were manipulated using Lecia NT software.

Agonist Mediated Down-regulation of the PAR1mut/GFP Fusion Protein Detected in a Plate Fluorimeter Cells were seeded into black 96 well view plates (Costar) the day before the experiment. The growth media was replaced with phenol red free DMEM/F12 (1:1) media containing 2 mM L-glutamine and either TRAP (10 μM–1 nM) or thrombin (1–0.0001 units/ml). The media also contained 0.5 mM Brilliant Black dye to absorb any media associated autofluorescence. Cells were incubated with compound for 4 hours at 37° C. and fluorescence was detected on the Tecan Spectrafluor Plus fluorimeter. To control for plate and media autofluorescence results were calculated by subtracting a blank plate reading from the fluorescence values obtained in drug treated cells.

EXAMPLE 7

Figure 16:
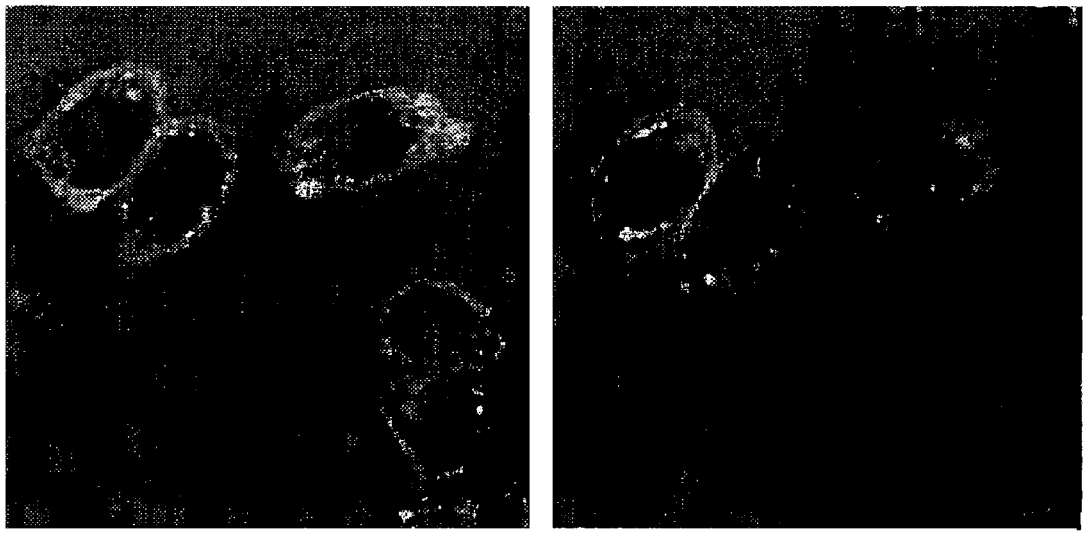
Figure 16:
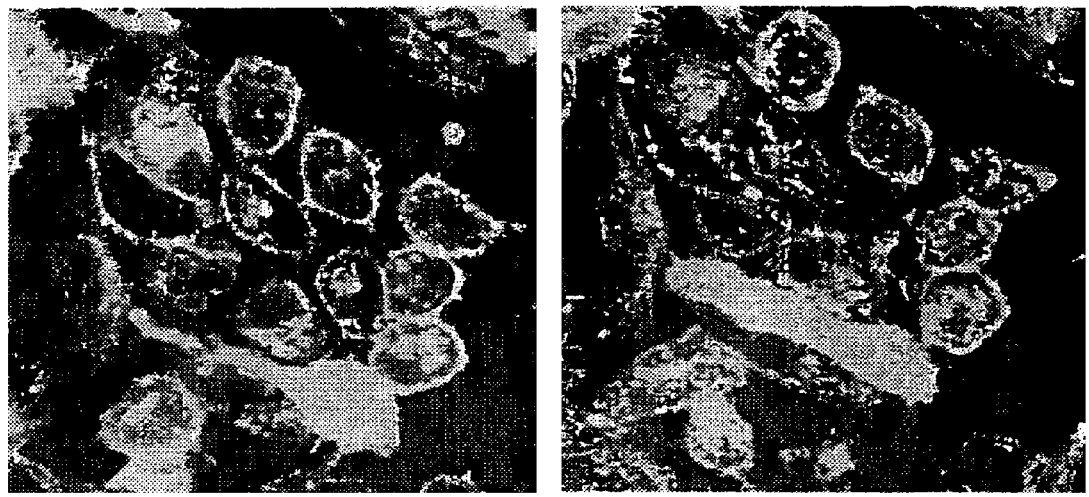

Construction of Mutated PAR1 Receptor Fused to GFP and Effect of PAR1 Agonist Ligand on its Cellular Localisation Results In HEK 293 cells stably transfected to express the PAR1/mut/GFP fusion protein GFP fluorescence is mainly localised to the cell membrane (FIG. 16). Some intracellular expression is also seen, which could represent protein synthesis and trafficking through the endoplasmic reticulum and golgi apparatus. After TRAP addition to cells the fusion protein slowly migrates away from the cell membrane into intracellular areas. Not all fluorescence is internalised and only a small proportion is degraded.

EXAMPLE 8

Agonist Down-regulation of the PAR1 mut/GFP Fusion Protein

Results

Figure 17:
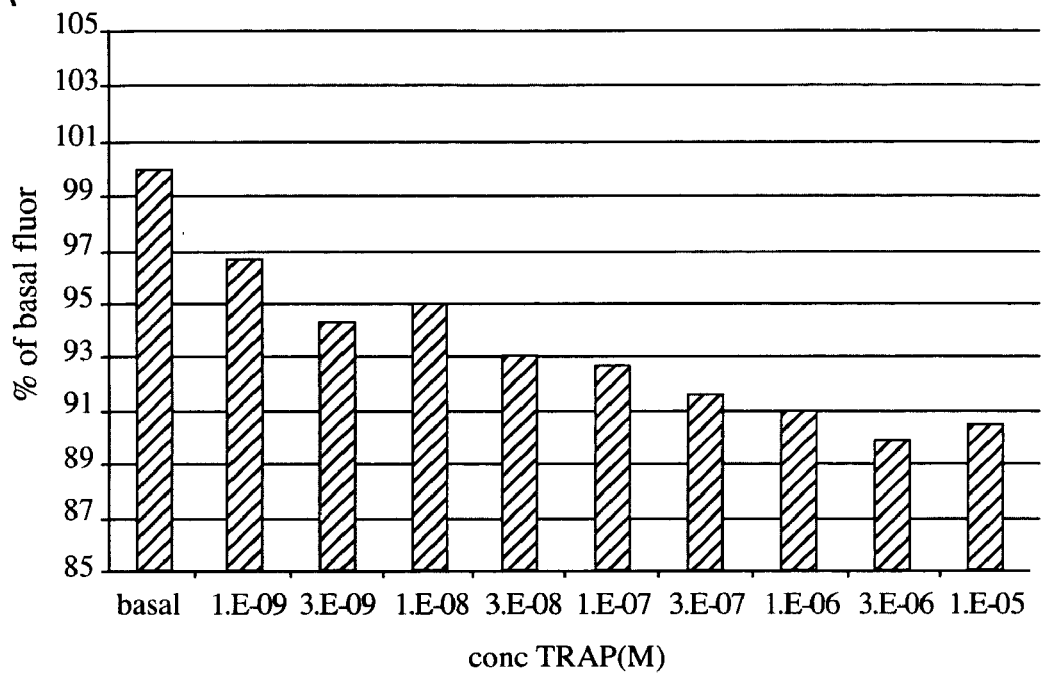
Figure 17:
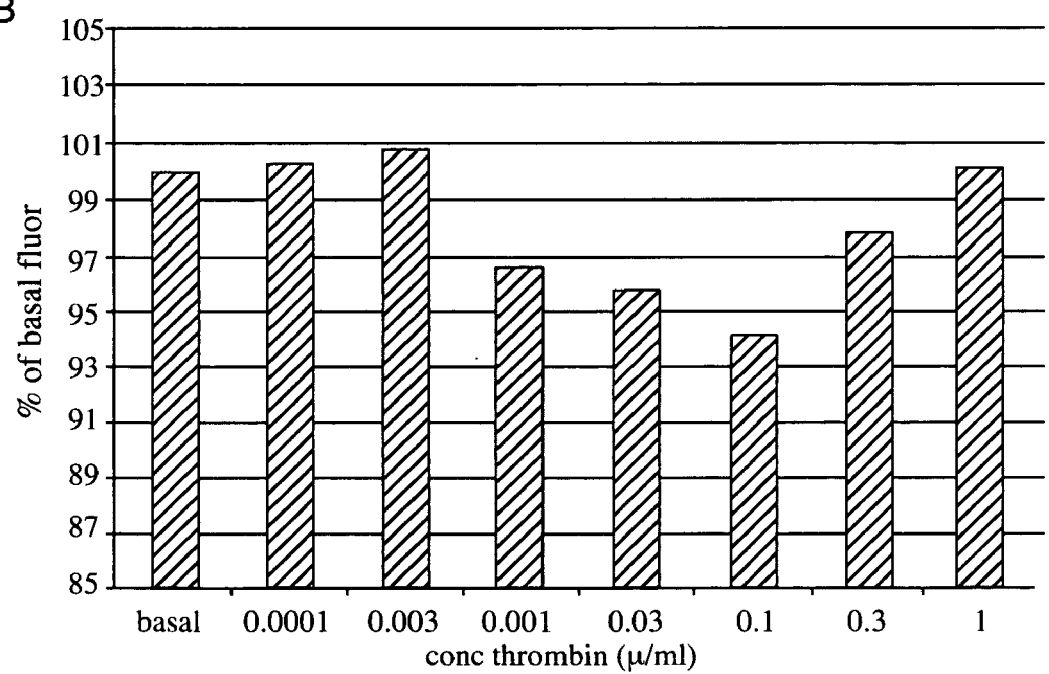

Both TRAP and thrombin caused a small down-regulation of the PAR1 mut/GFP construct when measured by plate fluorimeter after 4 hours incubation (FIG. 17). TRAP caused a dose related decrease in fluorescence which reached a maximum of about 20% loss in fluorescence and hence expression. The effect of thrombin was much less, only causing a maximum decrease of about 5%.

TABLE 1

Sequence of the oligonucleotides used in this study

| Sequence ID | Oligo name | Sequence |
|---|---|---|
| | NB100 | 5'-GCGCAGAGCCCGGGACAATG-3' |
| | NB101 | 5'-GCTGGATCCTTTTCCGAAGTTAACAGCTTTTTG-3' |
| | NB102 | 5'-CAGTTTGGGTCTGAATTGTGTC-3' |
| | NB103 | 5'-CTTTCAAGGCTAGGGTCGTCACGACCTCGTCCGC-3' |
| | NB104 | 5'-CCGGTGCAGGAGGTGCAAAAATGGATACCTGCTCTAGTAAC-3' |
| | NB105 | M13 forward primer (Stratagene) |

REFERENCES

Alam, J. and Cook, J. L. (1990). *Anal. Biochem.*, 188, 245–254.

Barak, L. S., Ferguson, S. S., Zhang, J., Martenson, C., Meyer, T., and Caron, M. G. (1997a) Mol. Pharmacol. 51, 177–184.

Barak, L. S., Stephen, S. G., Ferguson, J. Z. and Caron, M. G. (1997b). *J. Biol Chem,* 272, 27497–27500.

Chalfie, M. and Kain, S. R. (ed.) (1998). *Green fluorescent protein properties, applications and protocols.* Wiley Press.

Chen, W., Shields, T. S., Stork, P. J. S. and Cone, R. D. (1995). *Anal. Biochem.,* 226, 349–354.

DeWet, J. R., Wood, K. V., DeLuca, M., Helsinki, D. R. and Subramani, S. (1987). *Mol. Cell Biol.,* 7, 725–737.

Drmota, T., Gould, G. W., and Milligan, G. (1998a) J. Biol. Chem. 273, 24000–24008 Ferrer, J. C., Baque, S. and Guinovart, J. J. (1997). *FEBS Lett.,* 415, 249–252.

Freedman, N. J. and Lefkowitz, R. J. (1996) *Recent Prog. Horm. Res.* 51, 319–353.

Gether, U., Lin, S., Ghanouni, P., Ballesteros, J. A., Weinstein, H. and Kobilka, B. K. (1997a) EMBO J. 16, 6737–6747.
Gudermann, T., Kalkbrenner, F. and Schultz, G. (1996). *Ann. Rev. Pharmacol. Toxicol.*, 36, 429–59.
Haas, J., Park, E. C. and Seed, B. (1996). *Curr. Biol.*, 6, 315–324.
Henthorn, P., Zervos, P., Raducha, M., Harris, H. and Kadesch, M. (1988) *Proc. Natl. Acad. Sci. USA.*, 85, 6342–6346.
Javitch, J. A., Fu, D., Liapakis, G. and Chen, J. (1997) J. Biol. Chem. 272, 18546–18549.
Leurs, R., Smit, M. J., Alewijnse, A. E. and Timmerman, H. (1998) Trends Biochem. Sic. 23, 418–422.
Lorenz, W. W., McCann, R. O., Longiaru, M. and Cormier, M. J. (1991). *Proc. Natl. Acad. Sci. USA.*, 88, 4438–4442.
MacEwan, D. J. and Milligan, G. (1996a) Mol. Pharmacol. 50, 1479–1486.
Moore, J., Davis, S. and Dev, I. (1997). *Anal. Biochem.*, 247, 203–209.
Rees, S., et al., Biotechniques 20, 102–110; 1996).
Samama, P., Cotecchia, S., Costa, T. and Lefkowitz, R. J. (1993) J. Biol. Chem. 268, 4625–4636.
Samama, P., Pei, G., Costa, T., Cotecchia, S. and Lefkowitz, R. J. (1994) Mol. Pharmacol. 45, 390–394.
Scheer, A. and Cotecchia, S. (1997) J. Recept. Signal Transduct. Res. 17, 57–73. Stables, J., Green, A., Marshall, F., Fraser, N., Knight, E, Sautel, M., Milligan, G., Lee, M. and Rees, S.(1997). *Anal. Biochem.*, 252, 115–126.
Stratowa, C., Himmler, A. and Czernilofsky, C.(1995). *Curr. Op. Biotech.*, 6, 574–581.
Suto, C. M. and Ignar, D. M. (1997). *J. Biomolecular Screening*, 2, 7–9.
Trejo, J., Hammes, S. R. and Coughlin, S. R. (1998) Proc. Natl. Acad. Sci. USA. 95, 13698–13702.
Trejo, J and Coughlin, S. R. (1999) J. Biol. Chem. 274, 2216–224.
Shapiro, M. J. and Coughlin, S. R. (1998) J. Biol. Chem. 273, 29009–29014.
Vu, T.-K. H., Hung, D. T., Wheaton, V. I. and Coughlin, S. R. (1991) Cell 64, 1057–1068.
Vu, T.-K. H., Wheaton, V. I., Hung, D. T. and Coughlin, S. R. (1991) Nature 353, 674–677.
Walker, D. and De Waard, M. (1998). *Trends. Neurosci.*, 21, 148–154.
Wang, S. and Hazelrigg, T. (1994). Nature, 369, 400–403.
Wong, Y. G. (1994) Gi assays in transfected cells. *Methods Enzymol.* 238, 81–94.
Wise, A., Watson-Koken, M.-A., Rees, S., Lee, M. and Milligan, G. (1997) *Biochem. J.*, 321, 721–728.
Zernicka-Goetz, M., Pines, J., McLean Hunter, S., Dixon, J. P. C., Siemering, K. R., Haseloff, J., Evans, M. J. (1997) *Development* 124, 1133–1137.

What is claimed is:

1. An assay for detecting an effect a compound has on a membrane receptor, comprising the steps of:
    a) adding the compound to a cell expressing a membrane receptor/reporter fusion protein, the fusion protein comprising a membrane receptor segment and a reporter segment; and
    b) detecting any change of said receptor/reporter fusion protein by detecting a signal from the reporter segment; wherein the membrane receptor segment is a constitutively active mutant receptor.

2. The assay according to claim 1 wherein said assay is used to screen compounds for their effect on membrane receptors.

3. The assay according to claim 2 wherein any change is detected as an increase in activity of the reporter segment of the fusion protein.

4. The assay according to claim 1 wherein said assay is used to identify compounds that disrupt normal membrane receptor interactions.

5. The assay according to claim 1 for detecting a compound which serves as an inverse agonist, antagonist or agonist of the membrane receptor.

6. The assay according to claim 5 wherein said inverse agonist, antagonist or agonist of the membrane receptor is used in the study of receptor function.

7. The assay according to claim 1 wherein said membrane receptor is a G-protein coupled receptor.

8. The assay according to claim 1 wherein the membrane receptor/reporter fusion protein is initially unstable, such that the reporter activity is detected at a basal level and wherein after binding of a compound to the receptor segment of the fusion protein, the fusion protein is stabilized and an increase in reporter activity is observed.

9. The assay according to claim 7 wherein said G-protein coupled receptor is a serotonin receptor.

10. The assay according to claim 1 wherein the receptor/reporter fusion protein is expressed from nucleic acid construct comprising a gene encoding said reporter segment which is fused in-frame to the 5' or 3' end of a gene encoding said membrane receptor segment.

11. The assay according to claim 1 wherein the functionality of said membrane receptor segment is substantially unaffected by fusion of the reporter segment to the membrane receptor segment.

12. The assay according to claim 11 wherein said reporter segment is Green Fluorescent Protein (GFP), or active variant thereof.

13. The assay according to claim 12 wherein light emitted by said GFP protein is detected by fluorimetry, FACS, or microscopy techniques.

14. The assay according to claim 11 wherein said reporter segment is *Renilla reniformis* (sea pansy) luciferase protein.

15. The assay according to claim 14 wherein said reporter segment is luciferase which is detected in a microplate luminometer or using a CCD imaging system.

16. The assay according to claim 1 wherein the signal from said reporter segment is used to localize and/or quantify the membrane receptor segment.

17. An assay according to claim 16 wherein any change of said membrane receptor/reporter fusion protein is detected as a change in cellular localisation of the receptor/reporter fusion protein, or semi-quantitatively by the synthesis or degradation of said membrane receptor/reporter fusion protein.

18. An assay according to claim 1 wherein said detection of any change of said membrane receptor/reporter fusion protein is carried out with cells placed on the surface of a microscope slide.

19. The assay according to claim 1 wherein said detection of any change of said membrane receptor/reporter fusion protein is carried out on cells placed in a well of a microtitre plate.

20. An assay for detecting a test compound which has an effect on a membrane receptor, comprising the steps of
    a) expressing a membrane receptor/reporter fusion protein in a cell, wherein the fusion protein comprises a membrane receptor segment and a reporter segment, and wherein the membrane receptor segment is a constitutively active mutant receptor;
    b) detecting a basal level of reporter activity;
    c) adding a test compound to the cell; and
    d) detecting a resulting activity of the reporter segment, wherein alteration of reporter activity with respect to the basal level is due to the test compound having an effect on the membrane receptor segment.

* * * * *